US012669485B2

(12) United States Patent
Potyrailo et al.

(10) Patent No.: US 12,669,485 B2
(45) Date of Patent: Jun. 30, 2026

(54) SYSTEM AND METHOD FOR MULTI-GAS SENSING AT SEVERAL OPERATING TEMPERATURES

(71) Applicant: General Electric Company, Schenectady, NY (US)

(72) Inventors: Radislav Alexandrovich Potyrailo, Niskayuna, NY (US); Baokai Cheng, Schenectady, NY (US)

(73) Assignee: GE Infrastructure Technology LLC, Greenville, SC (US)

( * ) Notice: Subject to any disclaimer, the term of this patent is extended or adjusted under 35 U.S.C. 154(b) by 796 days.

(21) Appl. No.: 17/859,887

(22) Filed: Jul. 7, 2022

(65) Prior Publication Data

US 2024/0011962 A1    Jan. 11, 2024

(51) Int. Cl.
| | |
|---|---|
| *G01N 3/00* | (2006.01) |
| *G01N 27/12* | (2006.01) |
| *G01N 33/00* | (2006.01) |

(52) U.S. Cl.
CPC ....... *G01N 33/0032* (2013.01); *G01N 27/123* (2013.01)

(58) Field of Classification Search
CPC .. G01N 27/026; G01N 27/123; G01N 27/124; G01N 33/0004; G01N 33/0016;
(Continued)

(56) References Cited

U.S. PATENT DOCUMENTS

| | | | |
|---|---|---|---|
| 5,345,213 A | 9/1994 | Semancik et al. | |
| 9,618,491 B1 | 4/2017 | Kellaway et al. | |

(Continued)

FOREIGN PATENT DOCUMENTS

| | | |
|---|---|---|
| WO | 2011008043 A2 | 1/2011 |

OTHER PUBLICATIONS

Zhao, Wen-Jie, et al. "Optimized low frequency temperature modulation for improving the selectivity and linearity of SnO 2 gas sensor." IEEE Sensors Journal 20.18 (2020): 10433-10443. (Year: 2020).*

(Continued)

*Primary Examiner* — Robert J Eom

(74) *Attorney, Agent, or Firm* — Fletcher Yoder, P.C.

(57) ABSTRACT

A system and a method for multi-gas sensing using dielectric excitation of a single sensing material at multiple operating temperatures. By measuring dielectric excitation responses of the gas sensing material, enhanced multi-gas differentiation and differentiation can be achieved using fewer operating temperatures than would be used by the same MOS gas sensing material configured to perform multi-gas differentiation based on resistance responses alone. The disclosed gas sensors and gas sensing techniques enable improved response linearity, improved dynamic range, and reduced computational resource consumption for multi-gas quantitation relative to traditional resistance-based gas sensing methods. Present embodiments unexpectedly demonstrate MOS-based gas sensors that can differentiate between different gases using responses collected using at least two different operating temperatures, wherein this differentiation is superior in the differentiation between different gases and in baseline stability, as compared to the resistance response of the same gas sensing material at more than two operating temperatures.

11 Claims, 20 Drawing Sheets

(58) Field of Classification Search
    CPC ........... G01N 33/0032; G01N 33/0034; G01N
              33/004; G01N 33/0047; G01N 33/005
    See application file for complete search history.

(56)                    References Cited

U.S. PATENT DOCUMENTS

| | | |
|---|---|---|
| 10,966,657 B2 | 4/2021 | Potyrailo et al. |
| 10,996,210 B2 | 5/2021 | Potyrailo et al. |
| 2017/0138876 A1 | 5/2017 | Potyrailo et al. |
| 2020/0191761 A1 | 6/2020 | Potyrailo et al. |
| 2020/0386701 A1 | 12/2020 | Potyrailo et al. |
| 2020/0386728 A1 | 12/2020 | Potyrailo |
| 2021/0072175 A1 | 3/2021 | Potyrailo et al. |
| 2021/0109049 A1 | 4/2021 | Potyrailo |

OTHER PUBLICATIONS

Potyrailo, Radislav A., et al. "Extraordinary performance of semi-conducting metal oxide gas sensors using dielectric excitation." Nature Electronics 3.5 (2020): 280-289. (Year: 2020).*

Vergara, Alexander, et al. "Quantitative gas mixture analysis using temperature-modulated micro-hotplate gas sensors: Selection and validation of the optimal modulating frequencies." Sensors and Actuators B: Chemical 123.2 (2007): 1002-1016. (Year: 2007).*

Afridi, Muhammad Yaqub, et al. "A monolithic CMOS microhotplate-based gas sensor system." IEEE Sensors Journal 2.6 (2003):644-655. (Year: 2003).*

International Search Report & Written opinion for PCT Application No. PCT/US2023/026946, Mailed Sep. 12, 2023, 14 Pages.

Potyrailo et al., "Extraordinary performance of semiconducting metal oxide gas sensors using dielectric excitation," Nature Electronics, 2020, https://doi.org/10.1038/s41928-020-0402-3 , 59 Pages.

Lee, "Linear gas sensing with dielectric excitation," May 2020, vol. 3, Nature Electronics, pp. 239-240.

Potyrailo et al., "Multi-gas sensors based on dielectric excitation," GE Research, https://web.archive.org/web/20200812161514/https://www.ge.com/research/project/multi-gas-sensors-based-dielectric-excitation , Last accessed Oct. 5, 2022, 5 Pages.

Junter, et al., "A Critical Review of Solid State Gas Sensors," Journal of the Electrochemical Society, Last Accessed Feb. 20, 2020, 167, 037570, 31 Pages.

Hikita et al., "New Gas-Sensing Method for Detecting Carbon Monoxide by Use of the Complex Impedance of a CuO/ZnO Heterocontact under a dc Bias Voltage," Tokyo, Japan, vol. 77, No. 7, Sep. 10, 1993, pp. 1961-1964.

Weimar et al., "AC Measurements on Tin Oxide Sensors to Improve Selectivities and Sensitivities," Sensors and Actuators B 26-27, 1995, pp. 13-18.

Jeong et al., "Rational Design of Semiconductor-Based Chemiresistors and their Libraries for Next-Generation Artificial Olfaction," Advanced Materials, Sep. 15, 2020, 47 Pages.

Nakata et al., "Gas Sensing Based on a Nonlinear Response: Discrimination between Hydrocarbons and Quantification of Individual Components in a Gas Mixture," Analytical Chemistry, vol. 68, No. 13, Jul. 1, 1996, pp. 2067-2072.

Heilig et al., "Gas identification by modulating temperatures of SnO2—based thick film sensors," Dec. 2, 1996, Sensors and Actuators B 43 (1997), Tubingen, Germany, pp. 45-51.

Meier et al., "Detecting Chemical Hazards with Temperature-Programmed Microsensors: Overcoming Complex Analytical Problems with Multidimensional Databases" Annual Review of Analytical Chemistry vol. 2, 2009, 24 Pages.

Zhang et al., "A novel method in the gas identification by using WO3 gas sensor based on the temperature-programmed technique," Sensors and Actuators B 206(2015), http://dx.doi.org/10.1016/j.snb.2014.09.063 , pp. 220-229.

Wen et al., "A Gas Mixture Prediction Model Based on the Dynamic Response of a Metal-Oxide Sensor," Sep. 11, 2019, micromachines, doi:10.3390/mi10090598 , 11 pages.

* cited by examiner

130

140

180

190

192

210

212

240

242

1

SYSTEM AND METHOD FOR MULTI-GAS SENSING AT SEVERAL OPERATING TEMPERATURES

STATEMENT REGARDING FEDERALLY SPONSORED RESEARCH & DEVELOPMENT

This invention was made with Government support under contract 75D30118C02617 awarded by Centers for Disease Control and Prevention. The Government has certain rights in the invention.

BACKGROUND

The subject matter disclosed herein generally relates to gas sensing, and more specifically relates to gas sensing using metal oxide semiconductor (MOS) sensors.

Metal oxide semiconductor (MOS) sensors can be operated by measuring a single sensor response or sensor output, such as resistance. These MOS chemiresistors and are popular because of their ability to non-selectively detect numerous gases with the proper selection of the base semiconductor material and doping materials. In such gas-responsive chemiresistor, a change in resistance of the MOS sensing element is measured, and this change in resistance is proportional to the gas concentrations in a fluid sample. However, the limited differentiation of MOS gas-responsive chemiresistor has hindered the use of such sensor in certain multi-gas sensing applications. Additionally, to achieve at least some gas differentiation, traditional MOS-based gas sensors require resistance measurements be performed at more than one operation temperature, in particular using at least two different operating temperatures, which can, decrease the longevity of the sensor, and introduce undesirable effects on the electrical measurements. Additionally, for multi-gas analysis, traditional MOS gas sensors typically require resistance measurements be collected at a number of different operational temperatures (e.g., 3, 4, 5 or more temperatures), which can introduce delays in operation to wait for the completion of each thermal cycle, decrease the longevity of the sensor, and introduce undesirable effects on the electrical measurements. Furthermore, even with a number of different operating temperatures are utilized when performing such resistance measurements, traditional MOS sensors struggle to effectively differentiate different gases in a fluid sample due to undesirable issues associated with the resistance measurements, such as baseline instability and non-linear response patterns.

BRIEF DESCRIPTION

With the foregoing in mind, present embodiments are directed to a system and a method for multi-gas sensing using dielectric excitation of a sensing material using at least two different operating temperatures. Embodiments of the gas sensor disclosed herein implement a metal oxide semiconductor sensing material that is switched between the different operating temperatures, and dielectric excitation responses of the sensing material are measured at each of these operating temperatures while the sensing material is exposed to a fluid sample. The disclosed gas sensors and gas sensing methods unexpectedly provide desirable characteristics, such as enhanced multi-gas differentiation using fewer temperature switching steps, as compared to traditional MOS resistance-based gas sensors and gas sensing methods. For example, by measuring dielectric excitation responses of using a single gas sensing element switched between two operating temperatures, the disclosed embodiments demonstrate superior multi-gas differentiation compared to other gas sensors and other gas sensing methods that rely on resistance measurements collected at several (e.g., more than 2) different operating temperatures.

In an embodiment, a gas sensor system for multi-gas analysis of a fluid sample includes a gas sensing element configured to operate at multiple temperatures and to contact the fluid sample; a heating element coupled to the gas sensing element and configured to heat the gas sensing element; and a heater controller operatively coupled to the heating element and configured to control the heating element to heat the gas sensing element to each of the multiple temperatures while the gas sensing element contacts the fluid sample. The gas sensor system also includes a measurement circuit operatively coupled to the gas sensing element and configured to provide dielectric excitation to, and to measure dielectric excitation responses of, the gas sensing element while the gas sensing element is heated to each of the multiple temperatures and contacts the fluid sample, wherein the measured dielectric excitation responses provide enhanced differentiation between at least two gases in the fluid sample and improved response linearity to the at least two gases in the fluid sample as compared to resistance responses of the gas sensing element when contacting the fluid sample at each of the multiple temperatures.

In an embodiment, a method of operating a gas sensor for multi-gas analysis of a fluid sample includes exposing a gas sensing material of the gas sensor to the fluid sample; measuring, via a measurement circuit of the gas sensor, a first set of dielectric excitation responses of the gas sensing material while the gas sensing material is heated to a first temperature and exposed to the fluid sample; measuring, via the measurement circuit of the gas sensor, a second set of dielectric excitation responses of the gas sensing material while the gas sensing material is heated to a second temperature and exposed to the fluid sample; and receiving, via an on-board data processor of the gas sensor, the first set of dielectric excitation responses of the gas sensing material at the first temperature and the second set of dielectric excitation responses of the gas sensing material at the second temperature. The method also includes resolving, via the on-board data processor, at least two gases in the fluid sample based on at least a portion of the first set of dielectric excitation responses and at least a portion of the second set of dielectric excitation responses.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
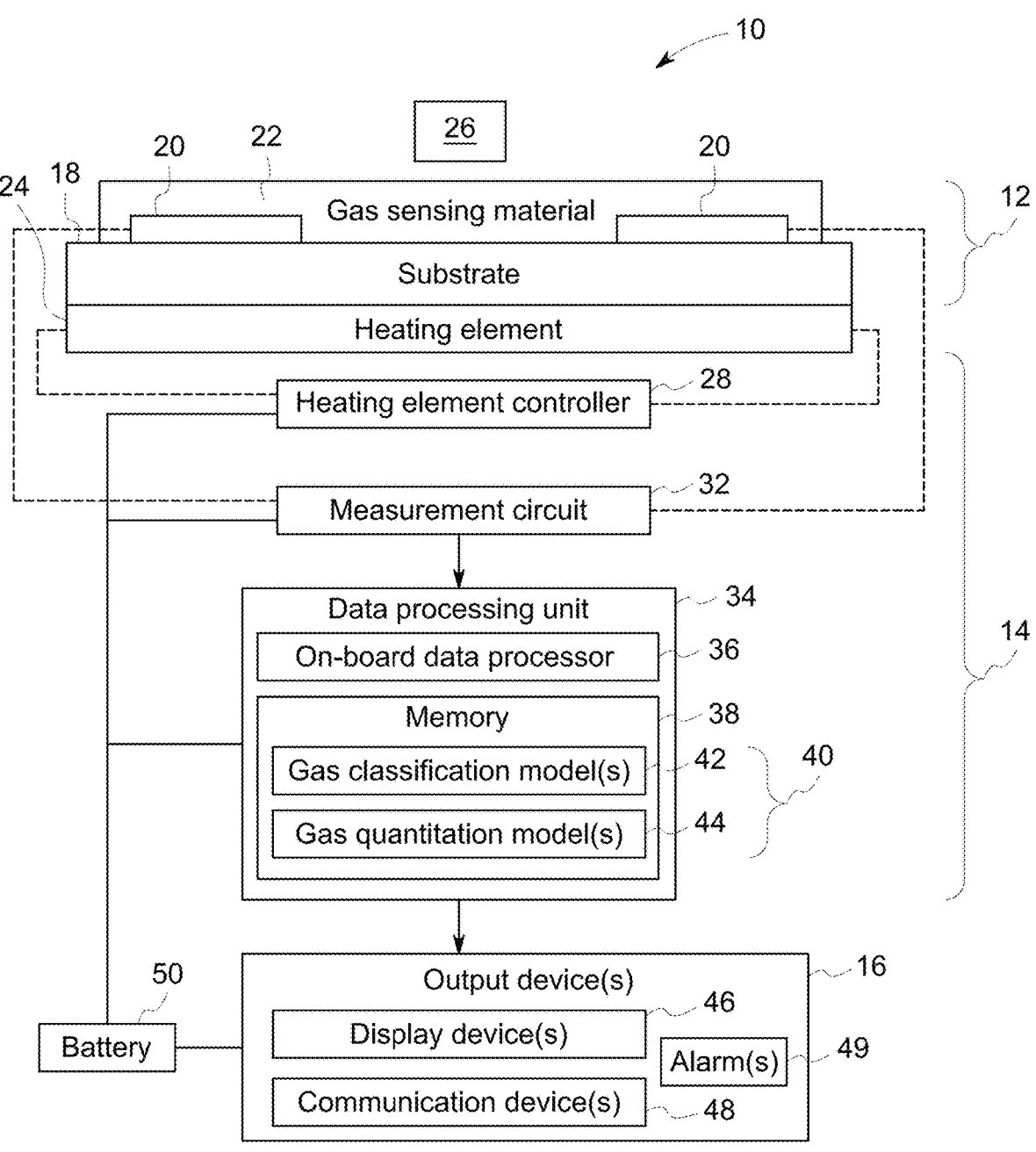
FIG. 1 is a schematic diagram of an embodiment of a gas sensor for multi-gas analysis of fluid samples, in accordance with aspects of the present technique.

Present embodiments are directed to a system and a method for multi-gas sensing using dielectric excitation of a single metal oxide semiconductor sensing material arranged as a single gas sensing element. It may be noted that metal oxide semiconductor sensing materials are often abbreviated in the industry as metal oxide semiconductor (MOS) materials or semiconducting metal oxide (SMOX) or semiconducting metal oxide (MOX) materials. Traditional MOS-based gas sensors measure only a direct current (DC) resistance response under a given excitation condition. A measurement of a single response per sensor under a given excitation condition is known as a single-output response or a single-output readout and the sensor is known as a single-output sensor. To differentiate multiple gases in a fluid sample, traditional MOS-based gas sensors measure DC resistance responses at several of different temperatures.

However, it is presently recognized that, by measuring dielectric excitation responses of the gas sensing material, enhanced multi-gas differentiation and resolution can be achieved using fewer operating temperatures than would be used by the same MOS gas sensing material configured to perform multi-gas differentiation based on resistance responses alone. Additionally, the disclosed gas sensors and gas sensing techniques enable improved response linearity, improved dynamic range, and reduced computational resource consumption for multi-gas quantitation relative to traditional resistance-based gas sensing methods. Furthermore, by reducing the number of operating temperature switching events, present embodiments enable gas sensors with improved measurement quality and enhanced operational lifetimes. That is, it is presently recognized that, using a set of predetermined operating temperatures, the dielectric relaxation spectrum of a gas sensing material is differently affected by different gases, and such desired differences are more pronounced as compared to the resistance response of the same gas sensing material, even when additional operating temperatures are used in the traditional resistance-based gas sensing methods. Thus, present embodiments unexpectedly demonstrate MOS-based gas sensors that can differentiate between different gases using dielectric excitation responses collected using at least two different operating temperatures, wherein this differentiation is superior in the differentiation between different gases and in baseline stability, as compared to the resistance response of the same gas sensing material at more than two operating temperatures.

As noted above, traditional MOS-based gas sensors typically measure DC resistance responses of a gas sensing material at several different operating temperatures when performing multi-gas analysis of a fluid sample. In contrast, present embodiments of gas sensors include a MOS-based gas sensing material that interacts with gases in a fluid sample at two or more operating temperatures and provides excitation responses to particular dielectric excitation frequencies, wherein these dielectric excitation responses of the gas sensing material are measured and analyzed to differentiate two or more gases in a fluid sample. As used herein, the terms "analyte", "analyte gas", or "analyte fluid" refer to a component of interest in the measured fluid. As used herein, the term "interferent", "interference gas", "interference fluid" refers to any component in the measured fluid that can undesirably affect the accuracy and precision of measurements of the analyte with the sensor.

With the foregoing in mind, FIG. 1 is a schematic diagram of an embodiment of a gas sensor 10 for multi-gas analysis of fluid samples, in accordance with the present technique. In different embodiments, the gas sensor 10 may be a wearable gas sensor, an ingestible gas sensor, or a tattooed gas sensor for personal (e.g., patient) monitoring. In certain embodiments, the gas sensor 10 may be an industrial environmental sensor, an asset monitoring sensor, an industrial process monitoring gas sensor, a consumer sensor, a transportation sensor, a security sensor, or any combination thereof.

For the embodiment illustrated in FIG. 1, the gas sensor 10 generally includes at least one gas sensing element 12, control circuitry 14, and one or more output devices 16. Each gas sensing element 12 includes a substrate 18 having sensing electrodes 20 disposed thereon, as well as a gas sensing material 22 (e.g., a suitably formulated metal oxide semiconductor material (MOS) applied to form a gas sensing film) disposed on the substrate 18 between the sensing electrodes 20. In certain embodiments, the gas sensor 10 may include multiple gas sensing elements 12 (e.g., an array of gas sensing elements 12), such as gas sensing elements having different MOS-based gas sensing materials 22. In certain embodiments, there may be more than two sensing electrodes 20, and the sensing electrodes 20 may include a plurality of interdigitated sensing electrodes. It may be appreciated that the gas sensing material 22 is generally applied onto the electrodes 20 to form the gas sensing film, such that the dielectric excitation of the gas sensing material 22, as well as the measurement of the dielectric excitation responses of the gas sensing material 22, is performed via the electrodes 20.

Additionally, a resistive heating element 24 is disposed on a surface of the substrate 18, opposite the gas sensing material 22, and is designed to heat the gas sensing material 22 to a suitable operating temperature during multi-gas analysis of a fluid sample 26. In certain embodiments, the heating element 24 may be disposed on a surface of the substrate 18 that is opposite the gas sensing material 22, while in other embodiments, the heating element 24 may be disposed on the same surface of the substrate 18 as the gas sensing material 22. For embodiments with multiple gas sensing elements 12, in certain cases, more than one gas sensing material 22 may be applied to a common substrate to form the multiple gas sensing elements 12 on a common substrate 18, which may be heated by a single heating element, while in other cases, each gas sensing material 22 may be disposed on a respective substrate 18 with a respective heating element 24. Additionally, in certain embodiments, the heating element 24 may be integrated into the substrate 18 as a monolithic structure.

During operation of the gas sensor 10, the gas sensing material 22 of the gas sensing element 12 is heated to each of a plurality of different operating temperatures as the gas sensing material 22 is exposed to the fluid sample 26, which may include two or more gases (e.g., an analyte gas and an interferent gas, at least two analyte gases). As such, the control circuitry 14 of the illustrated gas sensor 10 includes a heater controller 28 that is electrically connected to the heating element, and configured to control the heating element 24 and achieve the each of the different operating temperatures. For example, for an embodiment of the gas sensor 10 designed to measure excitation responses of the gas sensing material 22 at a first operating temperature and at a second operating temperature, the heater controller 28 may be configured to provide a first voltage to the heating element 24 to heat the gas sensing element 12 to the first operating temperature when a first set of dielectric excitation responses of the gas sensing material 22 are being measured, and to provide a second voltage to the heating element 24 to heat the gas sensing element 12 to the second operating temperature when a second set of dielectric excitation responses of the gas sensing material 22 are being measured. For example, in certain embodiments, the operating temperatures of the gas sensing material 22 may be between 30° C. and 1000° C., between 50° C. and 900° C., or between 80° C. and 600° C.

For the illustrated embodiment, the sensing electrodes 20 of the gas sensing element 12 are electrically coupled to a measurement circuit 32 of the control circuitry 14 of the gas sensor 10. The measurement circuit 32 is designed to provide at least dielectric (AC) excitation to the gas sensing material 22 at preselected frequencies and to measure dielectric responses of the gas sensing material 22 (e.g., impedance responses) to these excitations. In certain embodiments, the measurement circuit 32 may additionally be capable of (or designed to) provide direct current (DC) excitations to the gas sensing material 22 and to measure the DC responses (e.g., resistance responses) of the gas sensing material 22 to these excitations. In certain embodiments, the measurement circuit 32 may measure both AC and DC responses of the gas sensing material 22. However, in certain embodiments, the measurement circuit 32 may be designed to only provide dielectric excitation to, and only measure dielectric responses of, the gas sensing material 22.

As used herein, "dielectric excitation" of a MOS sensing material refers to an alternating current (AC) excitation of the MOS sensing material at a shoulder of its dielectric relaxation region. As used herein, "impedance" is a non-limiting term for any electrical response of the sensing system to an alternating electrical current applied to the gas sensing material 22. It may be appreciated that such a response may be measured as different electrical properties in different embodiments. Non-limiting examples of these electrical responses of the gas sensing material 22 to alternating electrical current include: impedance, real part of impedance, imaginary part of impedance, admittance, reactance, susceptance, or the like. In the present specification, examples of the responses are given as impedances; however, other electrical responses of the gas sensing material 22 to alternating electrical current excitation may be also equally produced. In one embodiment, the electrical response of the gas sensing material 22 may be monitored at the gas-modulated high-frequency shoulder of the dielectric relaxation peak of the sensing material. In one embodiment, the electrical response of the sensing system may be monitored at the gas-modulated low-frequency shoulder of the dielectric relaxation peak of the sensing material.

The gas sensor 10 may represent one or more different versions of multi-gas sensing systems described herein. In one or more embodiments, the measurement circuit 32 may include a resistor-capacitor (RC) electrical circuit that includes one or more resistor (R) and capacitor (C) components that may be electronically changed by a controller circuitry 14 by the presence of one or more analyte gases of interest. In one or more embodiments, the measurement circuit 32 may perform dielectric excitation and impedance measurements at one or more different frequencies or at one or more different RC configurations of the measurement circuit 32. For example, the measurement circuit 32 of the gas sensor 10 may measure impedance responses of the gas sensing material 22 at different frequencies, at different resistances of the RC electrical circuit of the measurement circuit 32, at different capacitances of the RC electrical circuit of the measurement circuit 32, or any combination of two or more therein. The measurement circuit 32 provides excitation and measurements of the response of the sensing element to gases. The measurement circuit is not designed to be affected by the measured gas concentrations. Rather, only the gas sensing element 12 is designed to be predictably affected by the measured gas concentrations.

The control circuitry 14 of the illustrated gas sensor 10 includes a data processing unit 34 (also referred to herein as data processing circuitry) that is communicatively coupled to the measurement circuit 32 to receive the excitation responses measured by the measurement circuit 32. The data processing unit 34 includes an on-board data processor 36, and includes a memory 38 storing gas analysis models 40, such as gas classification models 42, gas quantitation models 44, or any combination thereof. These gas analysis models 40 are mathematical models that generally store relationships between excitation responses (e.g., dielectric excitation responses) and particular classifications or concentrations of gases in a fluid sample. For example, the gas classification models 42 may store relationships between excitation responses of the gas sensing material 22 and particular classifications of gases at particular operating temperatures, while the gas quantitation models 44 may store relationships between excitation responses of the gas sensing material 22 and particular concentrations of gases at particular operating temperatures. In certain embodiments, the gas analysis models 40 may include one or more coefficients having values that are experimentally determined and stored in the memory 38. In some embodiments, the number of analyte gases determined by the gas classification models 42, or gas quantitation models 44, or any combination thereof, for the illustrated gas sensor 10 may range from one analyte gas to fifty analyte gases.

A gas sensing element that has two or more responses or outputs is called a multivariable gas sensing element. To analyze outputs from a multivariable gas sensing element, multivariate data processing principles are applied. Multivariate data processing principles can be applied to quantify diversity of responses of a multivariable sensor to different gases. Multivariate transfer functions can be built to quantify different gases. The built multivariate transfer functions can be implemented to quantify different gases in new measurement data from this multivariable gas sensing element. Non-limiting examples of multivariate data processing principles include methods to perform classification/cluster analysis and quantitation of gases. Classification/cluster analysis can be performed to correctly determine the type of the analyte gas. Quantitation can be performed to correctly determine the concentration of the analyte gas. Examples of classification/cluster analysis algorithms include, but are not limited, to Principal Component Analysis (PCA), Hierarchical Cluster Analysis (HCA), Independent Component Analysis (ICA), Linear Discriminant Analysis (LDA), and Support Vector Machines (SVM) algorithm. Non-limiting examples of methods for performing analyte quantitation to determine the concentration of a particular analyte gas include Principal Component Regression (PCR), Independent Component Regression (ICR), Nonlinear Regression Analysis (NRA), Discriminate Function Analysis (DFA), or Artificial Neural Network Analysis (ANN). In certain aspects of the inventive subject matter described herein, a classification algorithm can be followed by quantitation algorithm.

As discussed below, the on-board data processor 36 receives the excitation responses measured by the measurement circuit 32, selects particular excitation responses (e.g., dielectric excitation responses) for analysis, and provides these excitation responses as inputs to one or more of the stored gas analysis models 40, wherein the gas analysis models 40 return outputs that resolve or differentiate two or more gases in the fluid sample 26. As used herein, "resolving" two or more gases in a fluid sample, "providing resolution" between two or more gases in a fluid sample, "differentiating" two or more gases in a fluid sample, or "providing differentiation" between two or more gases in a fluid sample refers determining a respective classification for each of the gases in the fluid sample, determining a respective concentration of the gases in the fluid sample, or determining both respective classifications and respective concentrations of gases in the fluid sample. As used herein, "classifying" or "determining a classification of" an gas refers to determining an exact chemical identity (e.g., ethanol, acetone, hydrogen, carbon monoxide, methane, toluene, benzene) of the gas or determining a chemical class (e.g., a hydrocarbon, an oxide, a sulfide, a ketone, an aromatic hydrocarbon, and so forth) to which each gas belongs.

In certain embodiments, the memory 38 may be integrated into the on-board data processor 36. In certain embodiments, the on-board data processor 36 is a multicore processor. For example, in some embodiments, the on-board data processor 36 is a multicore processor on a single integrated circuit with two or more separate processing units (also referred to as cores), each of which reads and executes program instructions. In certain embodiments, the multicore processor may only include a single central processing unit (CPU) and multiple additional cores. For embodiments in which the on-board data processor 36 is a multicore processor, different gas analysis models and/or different signal processing algorithms may be independently executed by different cores to reduce the power consumption of the data processing unit 34 and/or the gas sensor 10.

For the illustrated embodiment, the gas sensor 10 includes one or more output devices 16. In certain embodiments, the output devices 16 include one or more display devices 46 that are configured to present information regarding a multi-gas analysis, such as the classification and/or concentration of two or more gases in the fluid sample 26. In some embodiments, other output devices 16 may include alarms 49, such as visual alarms (e.g., light emitting diodes (LEDs)), auditory alarms (e.g., speakers), and/or haptic alarms (e.g., haptic feedback devices). In certain embodiments, the output devices 16 may include one or more communication devices 48 (e.g., wired communication interfaces, wireless communication interfaces) that enable the gas sensor 10 to communicate with other computing systems, such as a desktop computer, a mobile computing device (e.g., a laptop, smart phone), a remote server (e.g., an Internet server, a cloud server), or other sensors (e.g., gas sensors, temperature sensors, vibration sensors, health monitors) of a multi-sensor monitoring system. For example, in certain embodiments, information determined by the on-board data processor 36 regarding the differentiation of two or more gases in the fluid sample 26 may be provided to an external computing system that serves as a controller of a mesh of sensors that includes the gas sensor 10. In some embodiments, the gas sensor may additionally or alternatively use the communication devices 48 to provide excitation response measurements to an external computing system, such that the external computing system can use these measurements to calculate one or more coefficient values for one or more of the gas analysis models and return these coefficient values to the gas sensor 10 for storage in the memory 38.

Additionally, the illustrated gas sensor 10 includes a battery 50 that is electrically coupled to provide power to various components of the gas sensor 10, including the control circuitry 14 and the output devices 16. It may be appreciated that the battery should have a suitable capacity to power all of the components of the gas sensor 10. For example, this may include: heating the gas sensing material 22, providing dielectric excitation to the gas sensing material 22, measuring the dielectric excitation responses of the gas sensing material 22, analyzing the measured dielectric excitation responses to differentiate two or more gases in a fluid sample, and presenting results of the analysis via a suitable output devices 16. In certain embodiments, the battery 50 may has a capacity that is sufficient to operate the gas sensor 10 for at least 10 hours. In some embodiments, the battery 50 may have a battery capacity between 1 milliamp-hour (mAh) and 500 mAh, or between 1 mAh and 200 mAh, or between 1 mAh and 100 mAh. In certain embodiments, such as embodiments in which the gas sensor 10 is designed to be particularly thin (e.g., for ingestible or tattooed embodiments of the gas sensor 10), the battery 50 may have a thickness less than about 5 millimeters (mm). In some embodiments, all of the components of the gas sensor 10 may be coupled to or at least partially disposed within a suitable packaging or housing for a particular gas sensing application. For example, for personal monitoring applications, the packaging of the gas sensor 10 may be made of a biocompatible polymer that can be externally worn, subcutaneously injected, or ingested to perform personal or patient multi-gas analysis.

The gas sensor 10 may be a wearable device that may be worn or move from one place to another by an operator. The gas sensor 10 may be positioned in or be an integrated part of a helmet, hat, glove, or other clothing attributes. For example, the gas sensor 10 may be held within a wearable or non-wearable transferable object, such as a frame of military or industrial eyeglasses, a wearable pulse oximeter, a safety vest or harness, an article of clothing, a mobile device (e.g., a cellular phone, a tablet, or the like), or the like. The wearable device may be integrated into a fabric of the clothing, can be positioned on clothing such as on a pocket, can be in a form of an arm band, worn on a wrist or other extremity, or the like. The wearable device may be worn by a subject, such as a human or animal or a robot, may be removably coupled or integrated with an article worn by a subject (e.g., a shirt, pants, safety vest, safety personal protection clothing, eyeglasses, hat, helmet, hearing device, or the like), or may be any alternative device that may be transferrable such that sensor can be moved between different positions, may be stationary or substantially stationary, or the like. The wearable device may be worn, or otherwise carried, by different subjects or individuals, such as, but not limited to, soldiers, medical professionals, athletes, system operators, students, otherwise active or inactive individuals, or the like. Optionally, the wearable sensing system may be coupled with, integrated with, disposed on, or the like, an asset, such as a moving system such as a drone, a stationary system, or the like. The wearable systems may be positioned on items worn by the subject, such as helmets, pockets (e.g., of shirts, pants, bags, or the like), gloves, arm bands, ear pieces, or the like, or may be attached or otherwise coupled directly to the subject or asset, such as on the wrist, around an ankle, or the like. The wearable device can be fabricated using manufacturing technologies based on complementary metal-oxide-semiconductor electronics, flexible electronics, flexible hybrid electronics and other known approaches to provide conformal and flexible designs, implementations, and use. Optionally, the gas sensor 10 may be a stationary device, may be independently mobile (e.g., detachable from an operator and capable of moving independent of the operator), may be airborne, or the like.

The gas sensor 10 may be in contact with the fluid 26 in the form of a fluid vessel that may be a form of a vessel with controlled volume, or in the form of an open area such as an indoor facility (e.g., a room, a hall, a house, a school, a hospital, a confined space, or the like), or in the form of an outdoor facility (e.g., a stadium, a gas-production site, fueling stations, gasoline fueling stations, hydrogen fueling stations, compressed natural gas fueling stations, liquefied natural gas fueling stations, gas distribution site, fuel distribution site, a seashore, a forest, a city, urban environment, marine environment, or the like). In one embodiment, the gas sensor 10 may provide continuous monitoring of the fluid 26 within the reservoir or flow path. In one or more embodiments, the gas sensor 10 may be an impedance gas sensor, an electromagnetic sensor, an electronic sensor, a hybrid sensor, or another type of sensor. Optionally, the gas sensor 10 may be part of a sensor array.

The fluid 26 may be a gas, a liquid, a gas-liquid mixture, a solid, particles or particulate matter, or the like, containing one or more analyte gases therein. In another embodiment, the fluid 26 may be a gas or fuel, such as a hydrocarbon-based fuel. One example of the fluid 26 is natural gas or hydrogen gas that is supplied to a powered system (e.g., a vehicle, airplane engine, or a stationary generator set) for consumption. Other examples of such a fluid 26 can include gasoline, diesel fuel, jet fuel or kerosene, bio-fuels, petro-diesel-biodiesel fuel blends, natural gas (liquid or compressed), and fuel oils. Another example of the fluid 26 is indoor or outdoor ambient air. Another example of the fluid 26 is air at an industrial, residential, military, construction, urban, and any other known site. Another example of the fluid 26 is ambient air with relatively small concentrations of benzene, naphthalene, carbon monoxide, ozone, formaldehyde, nitrogen dioxide, sulfur dioxide, ammonia, hydrofluoric acid, hydrochloric acid, phosphine, ethylene oxide, carbon dioxide, hydrogen sulfide, chemical warfare agents such as nerve, blister, blood, and choking agents, hydrocarbons and/or other pollutants. Another example of the fluid 26 is a disinfection agent, such as alcohol, aldehyde, chlorine dioxide, hydrogen peroxide. Another example of the fluid 26 is ambient air with relatively small concentrations, medium concentrations, and large concentrations of flammable or combustible gases such as methane, ethane, propane, butane, hydrogen, and/or other gases. Another example of the fluid 26 is at least one gas dissolved in an industrial liquid such as transformer oil, bioprocess media, fermentation media, wastewater, and any other. Another example of the fluid 26 is the at least one gas dissolved in a consumer liquid such as milk, non-alcoholic beverages, alcoholic beverages, cosmetics, and any other. Another example of the fluid 26 is at least one gas (e.g., a biomarker) dissolved in a body liquid such as blood, sweat, tears, saliva, urine, and any other.

In certain embodiments, the fluid 26 may include analyte gases that are toxic industrial materials or toxic industrial chemicals. A non-limiting list of example toxic industrial materials and chemicals includes, but is not limited to, ammonia, arsine, boron trichloride, boron trifluoride, carbon disulfide, chlorine, diborane, ethylene oxide, fluorine, formaldehyde, hydrogen bromide, hydrogen chloride, hydrogen cyanide, hydrogen fluoride, hydrogen sulfide, nitric acid (fuming), phosgene, phosphorus trichloride, sulfur dioxide, sulfuric acid, and tungsten hexafluoride. In certain embodiments, the fluid 26 may include analyte gases that are toxic materials of the medium Hazard Index. A non-limiting list of example toxic materials of the medium Hazard Index includes, but is not limited to: acetone cyanohydrin, acrolein, acrylonitrile, allyl alcohol, allylamine, allyl chlorocarbonate, boron tribromide, carbon monoxide, carbonyl sulfide, chloroacetone, chloroacetonitrile, chlorosulfonic acid, diketene, 1,2-dimethylhydrazine, ethylene dibromide, hydrogen selenide, methanesulfonyl chloride, methyl bromide, methyl chloroformate, methyl chlorosilane, methyl hydrazine, methyl isocyanate, methyl mercaptan, nitrogen dioxide, phosphine, phosphorus oxychloride, phosphorus pentafluoride, selenium hexafluoride, silicon tetrafluoride, stibine, sulfur trioxide, sulfuryl chloride, sulfuryl fluoride, tellurium hexafluoride, n-octyl mercaptan, titanium tetrachloride, trichloroacetyl chloride, and trifluoroacetyl chloride.

In certain embodiments, the fluid 26 may include analyte gases that are toxic materials of the low Hazard Index. A non-limiting list of example toxic materials of the low Hazard Index includes, but is not limited to: allyl isothiocyanate, arsenic trichloride, bromine, bromine chloride, bromine pentafluoride, bromine trifluoride, carbonyl fluoride, chlorine pentafluoride, chlorine trifluoride, chloroacetaldehyde, chloroacetyl chloride, crotonaldehyde, cyanogen chloride, dimethyl sulfate, diphenylmethane-4,40-diisocyanate, ethyl chloroformate, ethyl chlorothioformate, ethyl phosphonothioic dichloride, ethyl phosphonic dichloride, ethyleneimine, hexachlorocyclopentadiene, hydrogen iodide, iron pentacarbonyl, isobutyl chloroformate, isopropyl chloroformate, isopropyl isocyanate, n-butyl chloroformate, n-butyl isocyanate, nitric oxide, n-propyl chloroformate, parathion, perchloromethyl mercaptan, sec-butyl chloroformate, tert-butyl isocyanate, tetraethyl lead, tetraethyl pyrophosphate, tetramethyl lead, toluene 2,4-diisocyanate, and toluene 2,6-diisocyanate.

In certain embodiments, the fluid 26 may include analyte gases that are indoor pollutants. A non-limiting list of example indoor pollutants includes, but is not limited to:

acetaldehyde, formaldehyde, 1,3-butadiene, benzene, chloroform, methylene chloride, 1,4-dichlorobenzene, perchloroethylene, trichloroethylene, naphthalene, and polycyclic aromatic compounds. In certain embodiments, the fluid 26 may include analyte gases that are outdoor pollutants. A non-limiting list of example outdoor pollutants includes, but is not limited to: ozone, nitrogen dioxide, sulfur dioxide, and carbon monoxide.

Embodiments of the gas sensor 10 have the ability to differentiate gases at different concentrations in the fluid 26. For example, the gas sensor 10 may differentiate analyte gases at regulated vapor-exposure limits established by different organizations. In certain embodiments, the gas sensor 10 can resolve analyte gases below a Permissible Exposure Limit (PEL). In some embodiments, the gas sensor 10 can resolve analyte gases below Threshold Limit Value Short-Term Exposure Limit (TLV-STEL). In some embodiments, the gas sensor 10 may resolve analyte gases below Threshold Limit Value Time-Weighted Average (TLV-TWA). In some embodiments, the gas sensor 10 may resolve analyte gases below Immediately Dangerous to Life or Health (IDLH). In certain embodiments, the gas sensor 10 may resolve analyte gases below and above Lower Explosive Limit (LEL). In certain embodiments, the gas sensor 10 may be capable of resolving gases having a concentration less than 5%, less than 100 part-per-million (ppm), less than 100 part-per-billion (ppb), less than 100 part-per-trillion (ppt).

Figure 2:
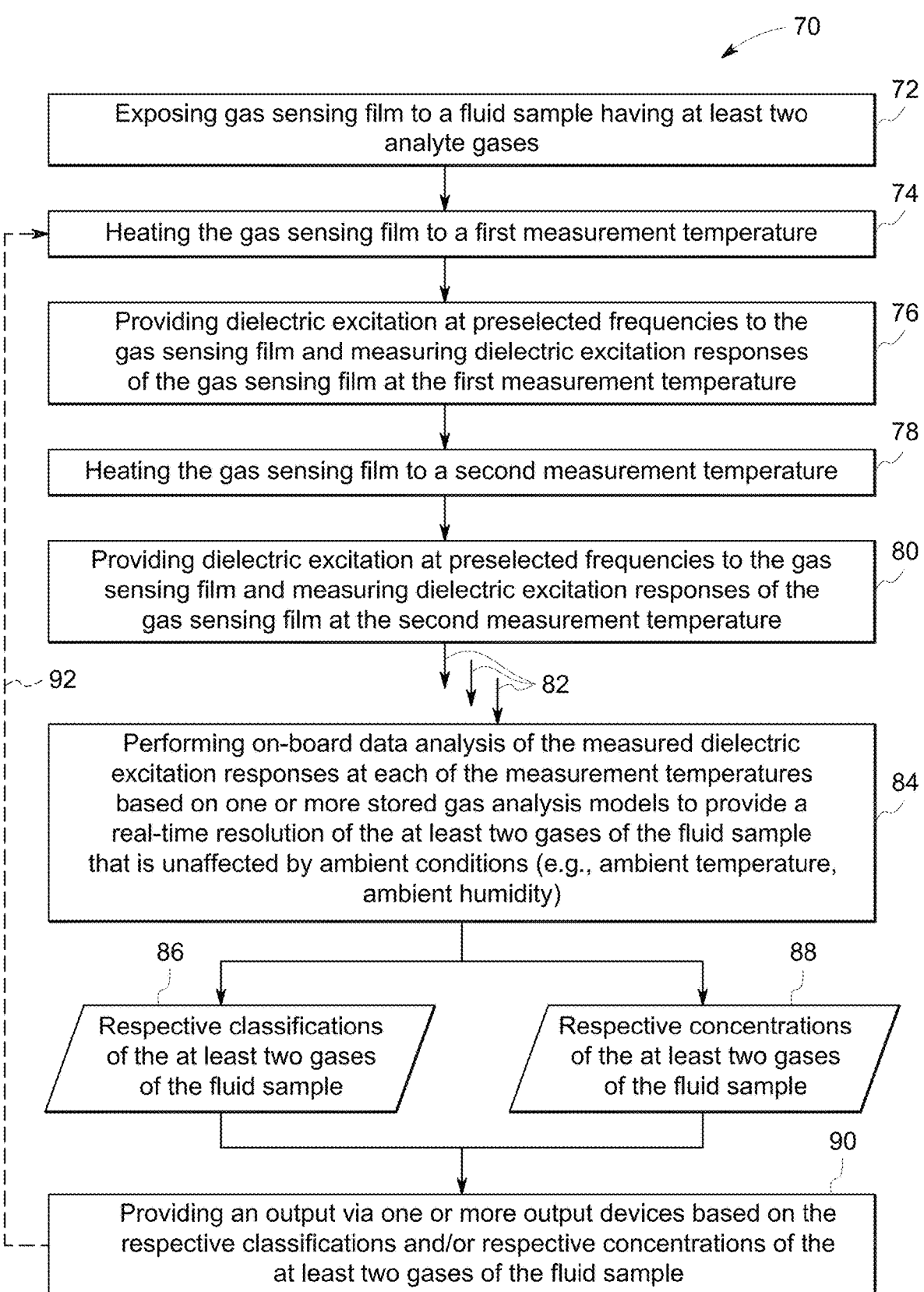
FIG. 2 is a flow diagram illustrating an embodiment of a process whereby the gas sensor performs multi-gas analysis, in accordance with aspects of the present technique.

FIG. 2 is a flow diagram illustrating an embodiment of a process 70 whereby the gas sensor 10 performs multi-gas analysis of a fluid sample 26. The process 70 begins with exposing (block 72) the gas sensing material 22 of the gas sensing element 12 to a fluid sample having at least two gases (e.g., at least two analyte gases, at least one analyte gas and one interference gas). For example, the entire gas sensor 10, or only the gas sensing material 22 of the gas sensor 10, may be exposed to the fluid sample. The process 70 includes heating (block 74) the gas sensing material 22 to a first operating temperature using the heater controller 28 and the heating element 24. Typically, the gas sensing material 22 is heated before, during, and after that it is exposed to the fluid sample 26.

Once the gas sensing material 22 has been exposed to the fluid sample 26 and heated to the first operating temperature, the process 70 proceeds with the measurement circuit 32 providing (block 76) dielectric excitation using at least two preselected frequencies to the gas sensing material 22 operating at the first operating temperature, and then measuring dielectric excitation responses (e.g., impedance responses) of the gas sensing material 22. In certain embodiments, the measurement circuit 32 may additionally apply DC excitation to the gas sensing material 22 and measure DC excitation responses (e.g., resistance responses) of the gas sensing material 22 at the first temperature. However, in some embodiments, the measurement circuit 32 may only measure dielectric excitation responses of the gas sensing material 22 as it contacts the fluid sample 26 at the first operating temperature. After measuring at least the dielectric responses of the gas sensing material 22 at the first operating temperature, the process 70 continues with heating (block 78) the gas sensing material 22 to a second operating temperature using the heater controller 28 and the heating element 24.

Once the gas sensing material 22 is heated to the second operating temperature while still being exposed to the fluid sample 26, the process 70 proceeds with the measurement circuit 32 providing (block 80) dielectric excitation using at least two preselected frequencies to the gas sensing material 22 operating at the second operating temperature, and then measuring dielectric excitation responses (e.g., impedance responses) of the gas sensing material 22. In certain embodiments, the measurement circuit 32 may additionally apply DC excitation to the gas sensing material 22 and measure DC excitation responses (e.g., resistance responses) of the gas sensing material 22 at the second temperature. However, in some embodiments, the measurement circuit 32 may only measure dielectric excitation responses of the gas sensing material 22 as it contacts the fluid sample 26 at the second operating temperature. It may be noted that, in other embodiments, such as a multi-gas analysis involving three or more gases, the process 70 may include any suitable number of addition steps in which the gas sensing material 22 is heated to another (e.g., a third, a fourth, a fifth, etc.) operating temperature, while the measurement circuit 32 measures at least the dielectric excitation responses of the gas sensing material 22, as generally indicated by the arrows 82 in FIG. 2.

Traditionally, MOS gas sensors 10 measure a DC resistance response of a MOS-based sensing element 12 and relate the measured DC resistance response to a concentration of a gas using a power-law relation between the measured resistance and gas concentration. Such DC resistance responses from a MOS gas sensor 10 may be provided as a signal output (e.g., to a user) in a form of an analog signal. Depending on the design of an analog circuit, an analog signal from a MOS gas sensor 10 may represent linear resistance, logarithmic resistance, or conductivity. Alternatively DC resistance responses from a traditional MOS-based gas sensor 10 may be provided as a signal output in a form of a digitized DC resistance response signal. Dependent upon the design of an analog/digital circuit, the digital signal from a MOS gas sensor 10 may be correlated with linear resistance, logarithmic resistance, or conductivity. A digital signal from a MOS gas sensor 10 that is correlated with its DC resistance response can be provided (e.g., to the user) by any of digital communication protocols, for example an I2C (Inter-Integrated Circuit), alternatively known as IIC, and any other communication protocols.

For the illustrated embodiment, the process 70 continues with the on-board data processor 36 of the gas sensor 10 performing (block 84) on-board data analysis of the measured dielectric excitation responses at each of the operating temperatures based on at least one of the stored gas analysis models 40 to provide a real-time differentiation or resolution of the gases in the fluid sample that is unaffected by ambient conditions (e.g., ambient temperature, ambient humidity). For certain embodiments in which the DC excitation response is also measured by the measurement circuit 32, the on-board data processor 36 may also provide the DC excitation response as inputs to at least one of the stored gas analysis models 40 when resolving the gases in the fluid sample. In this context, "real-time" refers to the on-board data processor 36 of the gas sensor 10 being able to locally, rapidly resolve or differentiate gases in the fluid sample without requiring the measured excitation responses be provided to an external computing system for processing.

For the embodiment of the process 70 illustrated in FIG. 2, after resolving the gases in the fluid sample 26, the gas sensor 10 may use one or more output devices 16 to provide an output (block 90) the respective classifications 86 of the gases in the fluid sample, the respective concentrations 88 of the gases in the fluid sample, or both. For example, one or more output devices 16 of the gas sensor 10 may present or display the respective classifications 86 and/or the respective concentrations 88 of the gases in the fluid sample 26. In certain embodiments, the gas sensor 10 may provide the respective classifications 86 and/or the respective concentrations 88 of the gases to an external computing system via one or more suitable communication devices 48 (e.g., a wireless communication interface) of the gas sensor 10. In certain embodiments, the gas sensor 10 may use one or more output devices 16 to output the respective alarms 49 of the presence of gases in the fluid sample above certain predetermined threshold levels stored in the memory 38 of the gas sensor 10. Additionally, in certain embodiments, the process 70 may proceed by returning to block 74 and repeating the remaining steps of the process 70 for a predetermined length of time or until a predetermined number of cycles, as indicated by the arrow 92.

Figure 3:
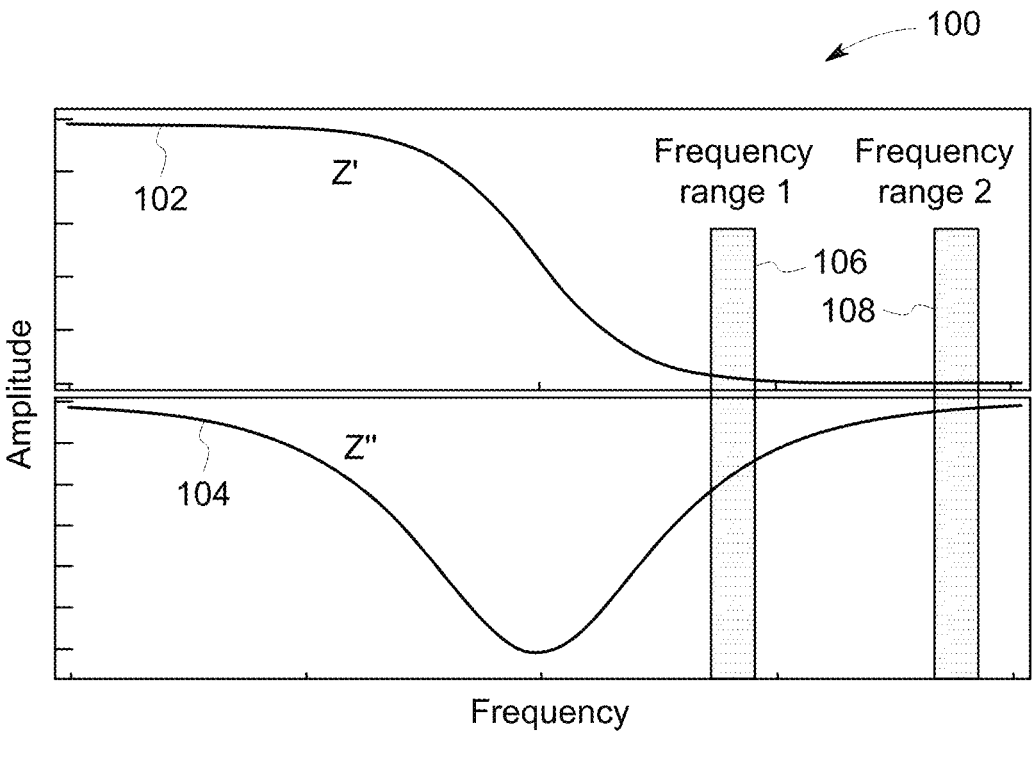
FIG. 3 is a graph of an example impedance spectrum of a gas sensing material of the gas sensor of FIG. 1 with preselected frequencies for dielectric excitation, in accordance with aspects of the present technique.

FIG. 3 is a graph illustrating an example impedance spectrum 100. In impedance spectroscopy, measurements of the real part $Z'$ and the imaginary part $Z''$ of the impedance may be performed over a broad range of frequencies to determine the shape of the impedance spectrum 100 of the gas sensor 10. As illustrated, the impedance spectrum includes two curves, each representing part of the impedance response of the gas sensor 10 over a broad range of frequencies to determine the shape of the impedance spectrum. In particular, a first curve 102 represents the real part ($Z'$) of the impedance of gas sensor 10, while a second curve 104 represents the imaginary part ($Z''$) of the impedance of the gas sensor 10 as measured over a broad range of frequencies. Unlike broad-band impedance spectroscopy measurements, the dielectric excitation measurements are performed over specific frequency ranges by following the front (high- or low-frequency) shoulder of the dielectric relaxation region obtained from impedance measurements of (n- or p-type, respectively) MOS materials when they are exposed to various gas concentrations.

For present embodiments, the measurement circuit 32 is or includes an impedance detector that measures the dielectric excitation response of the gas sensor 10 at two or more frequency ranges 106, 108 (which may or may not be disposed in the "dielectric relaxation region" of the gas sensor 10). For example, in certain embodiments, each dielectric excitation response measured by the measurement circuit 32 may include a combination (e.g., a sum, a difference, any other mathematical representation) of a value from the first curve 102 (e.g., a real impedance value) and a value from the second curve 104 (e.g., an imaginary impedance value), both selected from the frequency ranges 106, 108. Alternatively, in some embodiments, each dielectric excitation response measured by the measurement circuit 32 may include a combination (e.g., a sum, a difference, any other mathematical representation) of a value from the first curve 102 (e.g., a real impedance value $Z'$) and a value from the second curve 104 (e.g., an imaginary impedance value $Z''$), both selected from the frequency ranges 106, 108, or other frequency ranges.

Selection of the frequency ranges 106, 108 may depend on type of the gas sensing element 12 of the gas sensor 10. For example, related to the gas sensing element 12, the selection of the frequency ranges 106, 108 may depend on the type of the MOS sensing material, for example n-type or p-type or a combination of n- and p-type MOS sensing material and type of gases for measurements such of reducing gases or oxidizing gases. As a result, either the high-frequency shoulder region or the low-frequency shoulder region may be selected for measurements. For example, response at the frequency ranges 106, 108 may include data indicative of sensor response to gases in the fluid sample.

The identities and/or concentrations of gases in the fluid sample may then be determined based on the sensor response at the first and second frequency ranges 106, 108.

Alternatively, in some embodiments, each dielectric excitation response measured by the measurement circuit 32 may include a combination (e.g., a sum, a difference, any other mathematical representation) of a value from the first curve 102 (e.g., a real impedance value) and a value from the second curve 104 (e.g., an imaginary impedance value), both selected from the frequency ranges 106, 108, or other frequency ranges. Selection of the frequency ranges 106, 108 may depend on the type of the MOS sensing material, for example n-type or p-type or a combination of n- and p-type MOS sensing material and type of gases for measurements such of reducing gases or oxidizing gases. As a result, either the high-frequency shoulder region or the low-frequency shoulder region may be selected. For example, response at the frequency ranges 106, 108 may include data indicative of sensor response to gases in the fluid sample. The identities and/or concentrations of gases in the fluid sample may then be determined based on the sensor response at the first and second frequency ranges 106, 108.

It may be appreciated that, for present embodiments, the dielectric excitation measurements represented in FIG. 3 are performed using at least two different operating temperatures. While the disclosed gas sensing element 12 still experiences temperature switching events during multi-gas analysis, it is presently recognized that the number of temperature switching events (also referred to herein as temperature steps) is reduced compared to when the same gas sensing element is used for only resistance-based multi-gas analysis. It may be appreciated that there are numerous advantages to reducing the number of temperature steps for multi-gas analysis. For example, in certain embodiments, since the gas sensor 10 utilizes fewer temperature steps for multi-gas analysis than a traditional resistance-based MOS gas sensor, the measurement circuit 32 spends less time waiting for the for the gas sensing material 22 to reach a particular temperature after switching operating temperatures, resulting in faster and more efficient operation relative to traditional MOS-based gas sensors, as well as more stable and reproducible results. Additionally, it is presently recognized that the continual temperature cycling of traditional MOS-based gas sensors undesirably ages heating elements and limits the operational lifetime of these sensors. As such, it is recognized that, by reducing the number of temperature steps, the disclosed gas sensor 10 demonstrates enhanced operational lifetime or longevity as compared to a traditional resistance-based MOS gas sensor. Furthermore, it is recognized that reducing the number of temperature steps also improves the quality of the electrical measurements by reducing undesirable noise and hysteresis that are associated with temperature switching. Moreover, it is presently recognized that, for the disclosed gas sensor 10, the dielectric excitation response at certain frequencies of the sensor dielectric relaxation spectrum provides a superior multi-gas differentiation and baseline stability, as compared to the resistance response of the same gas sensing element 12, even when a greater number of operating temperatures are used.

Experimental Example 1

To further demonstrate the superior performance of the disclosed technique, a first set of experiments was performed to compare the ability of conventional resistance measurements versus dielectric excitation measurements for the differentiation between two different analyte gases in fluid samples. For the first set of experiments, all measurements were performed using a metal-salt-doped tin oxide ($SnO_2$) as the gas sensing material 22. The measurements were performed by the measurement circuit 32 as either DC excitation responses (e.g., resistance measurements), or as dielectric excitation responses (e.g., impedance measurements) selected from the high-frequency shoulder region 106 or 108 of corresponding impedance spectrum 100 after dielectric excitation. Each excitation response measurement was performed with a heating element voltage from the heater controller of 1.6 volts (V) and 2.4 volts (V). For the embodiment of the gas sensor 10 used for these experiments, the 1.6 V heating element voltage corresponded to an operating temperature of approximately 250 degrees Celsius (° C.), while the 2.4 V heating element voltage corresponded to an operating temperature of approximately 350° C.

Figure 4A:
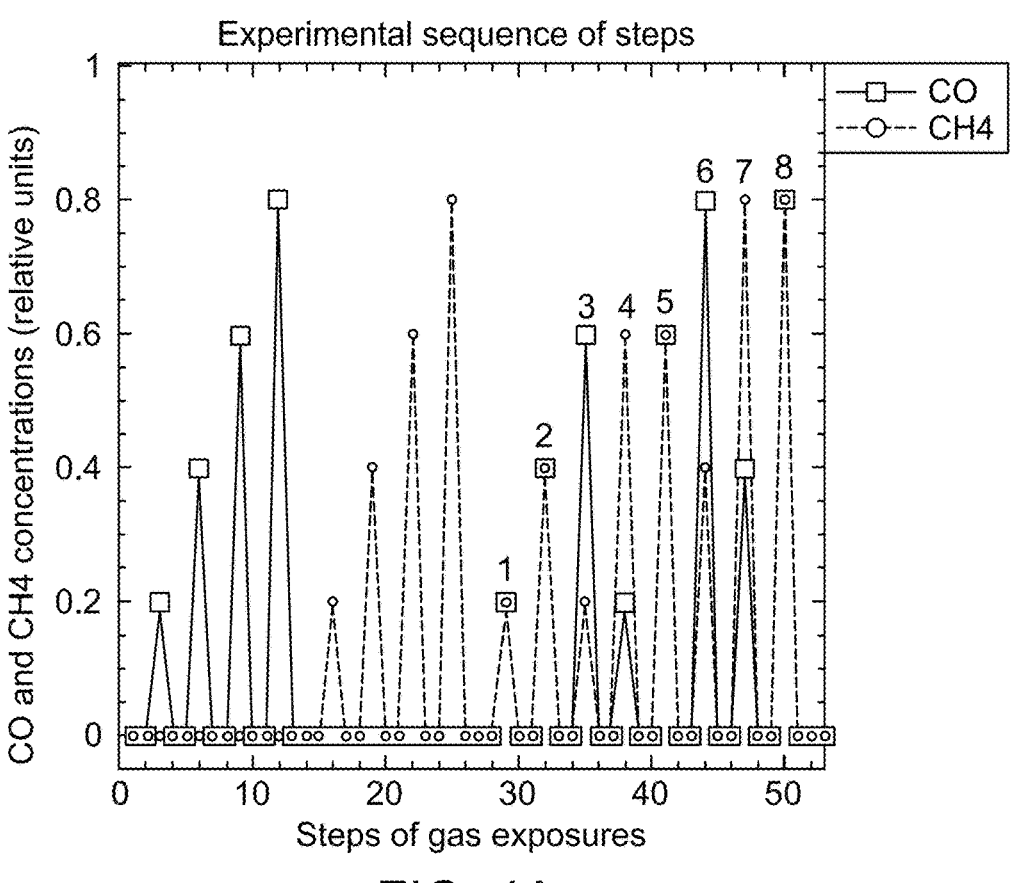
FIGS. 4A and 4B are plots illustrating the experimental sequence of steps and the experimental plan of the first experimental example, in accordance with aspects of the present technique.
Figure 4B:
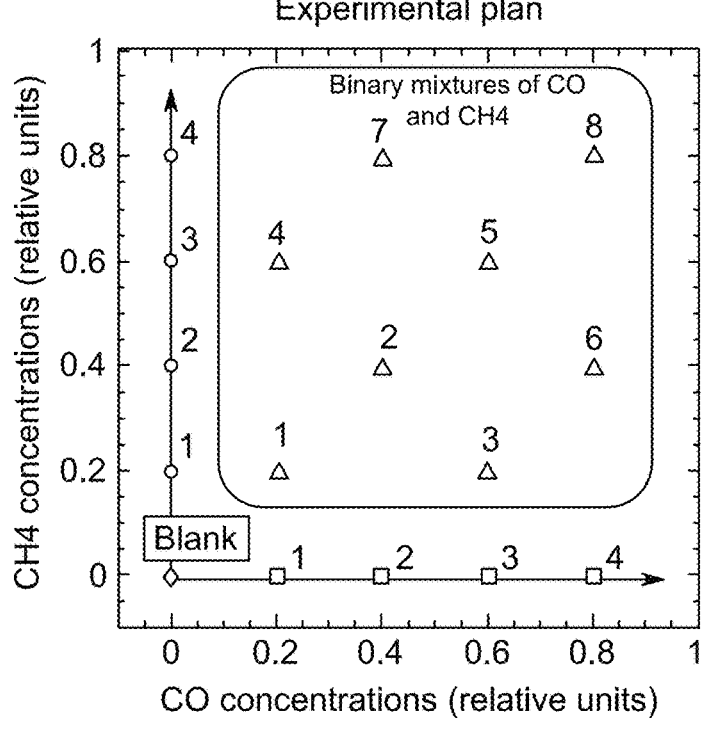

As illustrated in FIGS. 4A and 4B, for a first set of experiments, the gas sensor was exposed to each two different analyte gases at four different concentrations, as well as binary mixtures of the two analyte gases at 8 different ratios. The first analyte gas was carbon monoxide (CO), and the four different concentrations of the first analyte gas were: 160 parts-per-million (ppm), 320 ppm, 480 ppm, and 640 ppm, which are respectively illustrated in FIGS. 4A and 4B as 0.2, 0.4, 0.6, and 0.8. The second analyte gas was methane gas ($CH_4$), and the four different concentrations of the second analyte gas were: 800 ppm, 1600 ppm, 2400 ppm, and 3200 ppm, which are respectively illustrated in FIGS. 4A and 4B as 0.2, 0.4, 0.6, and 0.8. As such, for the experiments illustrated by FIG. 4, the gas sensor 10 was: (A) exposed to each of the four concentrations of the first analyte gas while resistance responses and impedance responses were collected at each operating temperature, (B) exposed to each of the four concentrations of the second analyte gas while resistance responses and impedance responses were collected at each operating temperature, and then (C) exposed to each of the 8 binary mixtures of the first and second analyte gases while resistance responses and impedance responses were collected at each operating temperature.

Figures 5A, 5B:
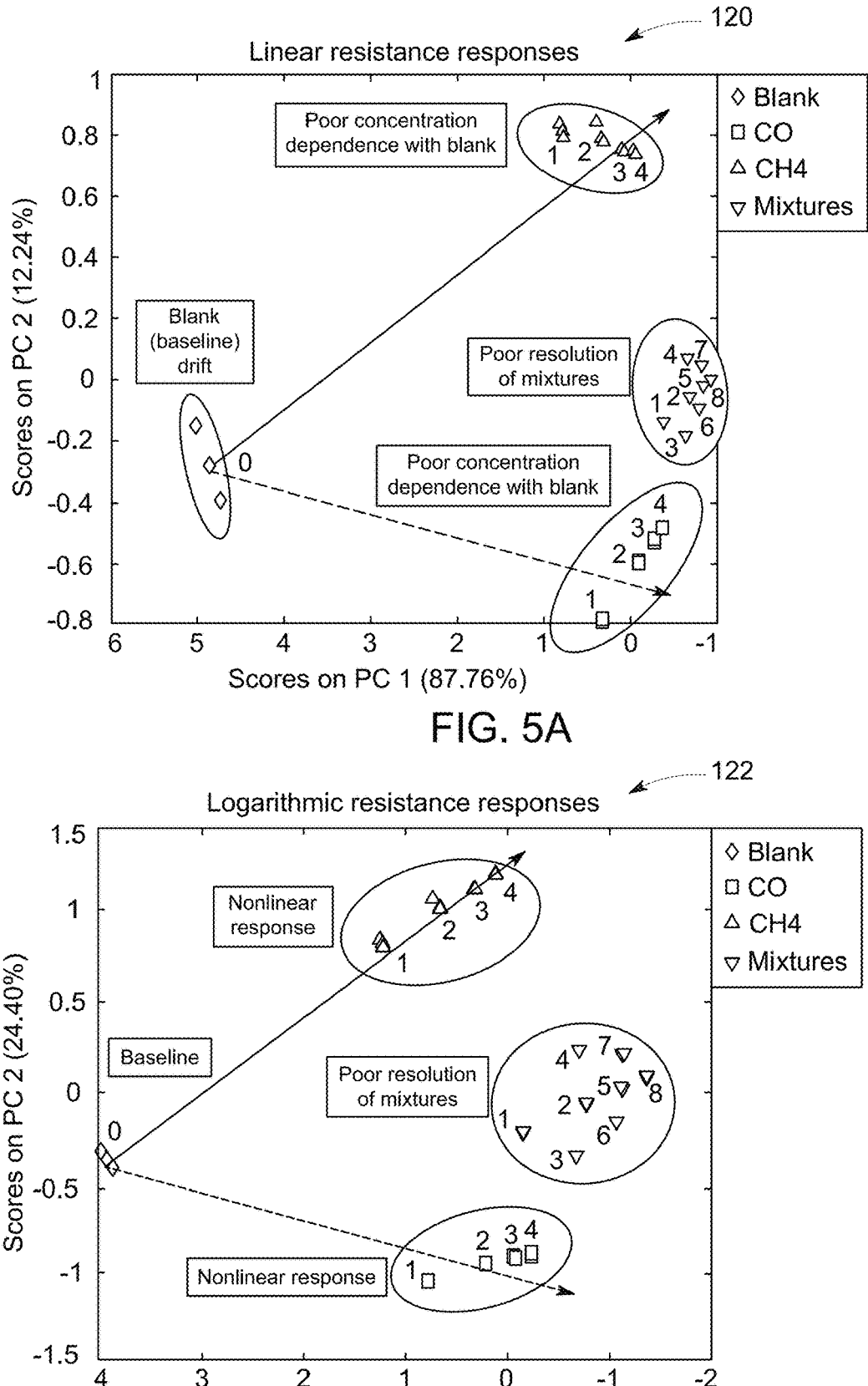
FIG. 5A is a scores plot illustrating the results of principal component analysis (PCA) for the analysis of linear resistance responses of the gas sensing material from the first experimental example, in accordance with aspects of the present technique.
FIG. 5B is a scores plot illustrating the results of PCA for the analysis of the logarithmic resistance responses of the gas sensing material from the first experimental example, in accordance with aspects of the present technique.

Principal component analysis (PCA) was applied to analyze resistance responses (e.g., DC excitation responses) for the experiment described by FIG. 4 to determine the ability of the gas sensor 10 to differentiate between the two analyte gases using two operating temperatures. For each sensor state (different concentrations of two analyte gases and a blank), three data points were extracted from the raw dynamic response at the steady-state or maximum signal change of the sensor response. FIGS. 5A and 5B depict the results of PCA as scores plots of the first two principal components (PC1 versus PC2). More specifically, FIG. 5A is a scores plot 120 illustrating the results of PCA for the analysis of linear resistance responses, while FIG. 5B is a scores plot 122 illustrating results of the PCA for the analysis of the logarithmic resistance responses.

As illustrated by the scores plot 120 FIG. 5A, the analysis of the linear resistance responses by PCA indicates that the resistance measurements did not provide a desired multi-gas differentiation with adequate gas-response linearity and baseline stability. For example, as noted in the illustration, the measured DC excitation responses did not correlate well with the concentrations of the first and second analyte gases. Additionally, for the binary mixtures, the first and second analyte gases were not adequately differentiated (e.g., discriminated, discerned, resolved) from one another. Moreover, in FIG. 5A, the baseline instabilities in the raw resistance responses were significantly pronounced in PCA scores plot as the spread between those data points.

As illustrated by the scores plot 122 of FIG. 5B, the analysis of the logarithmic resistance responses by PCA demonstrates some improvement relative to the analysis of the linear resistance responses of FIG. 5A. For example, in FIG. 5B, the measured DC excitation response upon exposure to the second analyte gas was more strongly correlated with the concentration of the second analyte gas than was observed in FIG. 5A; however, the correlation demonstrated substantial non-linearity. Additionally, while baseline drift was still observed in FIG. 5B, the baseline instabilities were less pronounced than those observed in FIG. 5A. However, in the scores plot 122 of FIG. 5B, the binary mixtures of the first and second analyte gases were still not adequately differentiated or resolved from one another. As such, the analysis of the logarithmic resistance responses still did not provide a desired multi-gas differentiation with desirable gas-response linearity and baseline stability.

Figure 6:
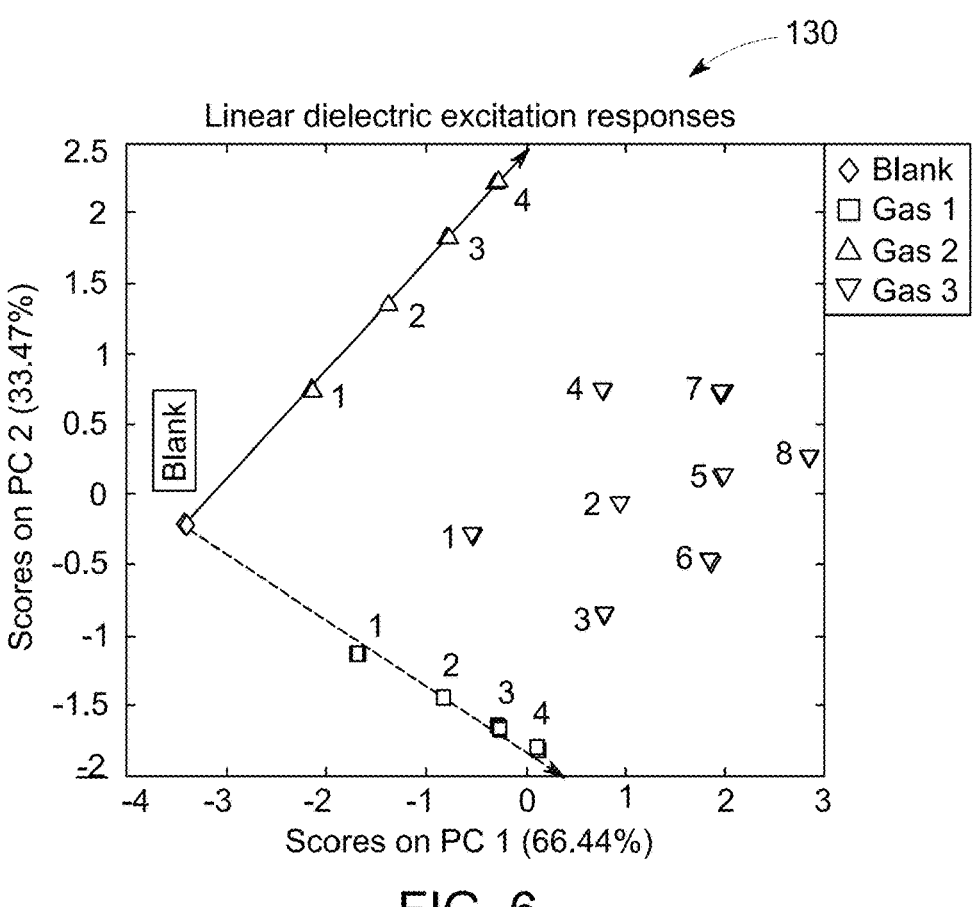
FIG. 6 is a scores plot illustrating the results of PCA for the analysis of the dielectric excitation responses of the gas sensing material from the first experimental example, in accordance with aspects of the present technique.

For comparison to the resistance measurements and analysis, PCA was also applied to analyze the dielectric excitation responses (e.g., impedance responses) for the first set of experiments described by FIG. 4 to determine the ability of the gas sensor 10 to differentiate between the two analyte gases using the two operating temperatures. FIG. 6 is a scores plot 130 depicting PCA results of the first two PCs (PC1 versus PC2) of the dielectric excitation responses of the gas sensing material 22 when operated at the two operating temperatures. In FIG. 6, the scores plot 130 demonstrates a clear differentiation between the two analyte gases, including the binary mixtures, and demonstrates a high degree of linearity in the correlation between the dielectric excitation responses and the concentrations of the analyte gases. For example, in the scores plot 130 of FIG. 6, the dielectric excitation responses for the blank form a tight cluster, and each of the dielectric excitation responses for the analyte gases form relatively linear trends that align with the blank samples. As such, unlike the DC excitation responses represented in FIGS. 5A and 5B, the scores plot 130 of FIG. 6 unexpectedly demonstrates a strong correlation or proportional relationship with a high degree of linearity between the dielectric excitations responses of the gas sensing material 22 and the respective concentrations of the two analyte gases when two operating temperatures are used.

Experimental Example 2

To further demonstrate the superior performance of the disclosed technique, a second set of experiments was also performed to compare the ability of conventional resistance measurements versus dielectric excitation measurements for the differentiation between three different analyte gases in fluid samples at two operating temperatures. For the second set of experiments, all measurements were performed using a metal-salt-doped tin oxide ($SnO_2$) as the gas sensing material 22. The measurements were performed by the measurement circuit 32 as either DC excitation responses (e.g., resistance measurements), or as dielectric excitation responses (e.g., impedance measurements) selected from the high-frequency shoulder region 106 or 108 of corresponding impedance spectrum 100 after dielectric excitation. Each excitation response measurement was performed with a heating element voltage of 6.5 V (corresponding to a first operating temperature), and also performed with a heating element voltage of 7.5 V (corresponding to a second operating temperature). For the embodiment of the gas sensor 10 used for these experiments, the 6.5 V heating element voltage corresponds to an operating temperature of approximately 250 degrees Celsius (° C.), while the 7.5 V heating element voltage corresponds to an operating temperature of approximately 285° C.

For the second set of experiments, the gas sensor 10 was exposed to each three different analyte gases at four different concentrations. The first analyte gas was toluene vapor, and the four different concentrations of the first analyte gas were: 8 ppm, 16 ppm, 24 ppm, and 32 ppm. The second analyte gas was acetone vapor, and the four different concentrations of the second analyte gas were: 8 ppm, 16 ppm, 24 ppm, and 32 ppm. The third analyte gas was benzene vapor, and the four different concentrations of the third analyte gas were: 8 ppm, 16 ppm, 24 ppm, and 32 ppm. As such, for the second set of experiments, the gas sensor 10 was: (A) exposed to each of the four concentrations of the first analyte gas while resistance responses and impedance responses were collected at each operating temperature, and then (B) exposed to each of the four concentrations of the second analyte gas while resistance responses and impedance responses were collected at each operating temperature.

Figure 7:
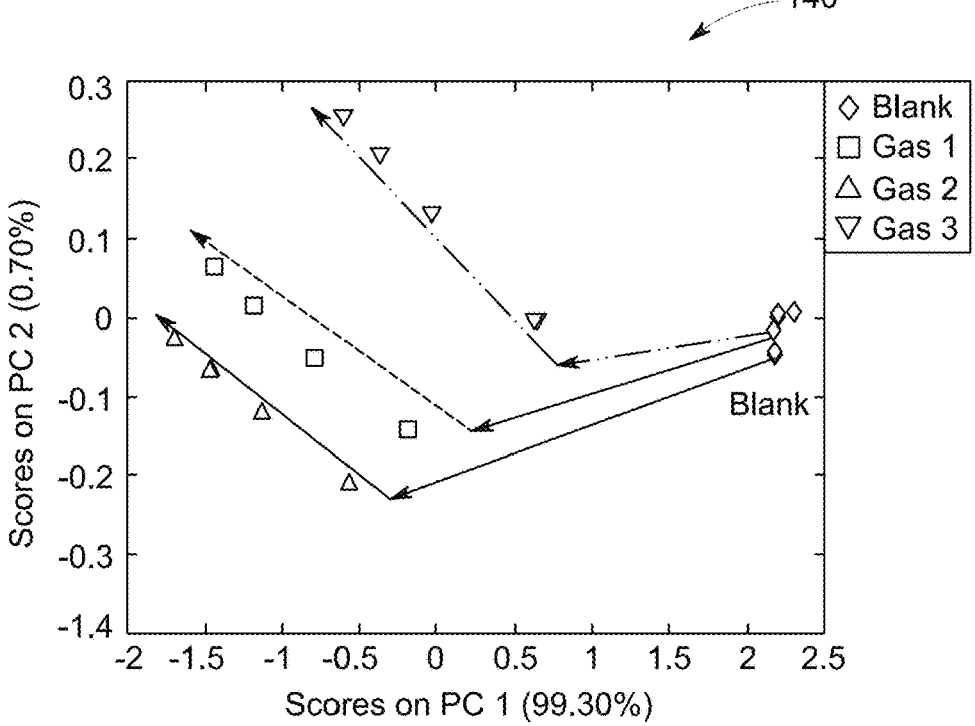
FIG. 7 is a scores plot depicting the results of PCA for the analysis of the logarithmic resistance responses of the gas sensing material from the second experimental example, in accordance with aspects of the present technique.

PCA was applied to analyze resistance responses (e.g., DC excitation responses) for the second set of experiments to determine the ability of the gas sensor 10 to differentiate between the three analyte gases using the two operating temperatures. For each sensor state (different concentrations of two analyte gases and a blank), three data points were extracted from the raw dynamic response at the steady-state or maximum signal change of the sensor response. FIG. 7 is a scores plot 140 depicting the results of PCA of the first two principal components (PC1 versus PC2) for the analysis of the logarithmic resistance responses. Analysis of logarithmic resistance responses by PCA shows differentiation between three gases with some significant non-linearity in the measured DC excitation responses. Also, in the scores plot 140 of FIG. 7, the baseline instabilities in the raw resistance responses were pronounced in PCA scores plot as the spread between the data points of the baseline (blank) response.

Figure 8A:
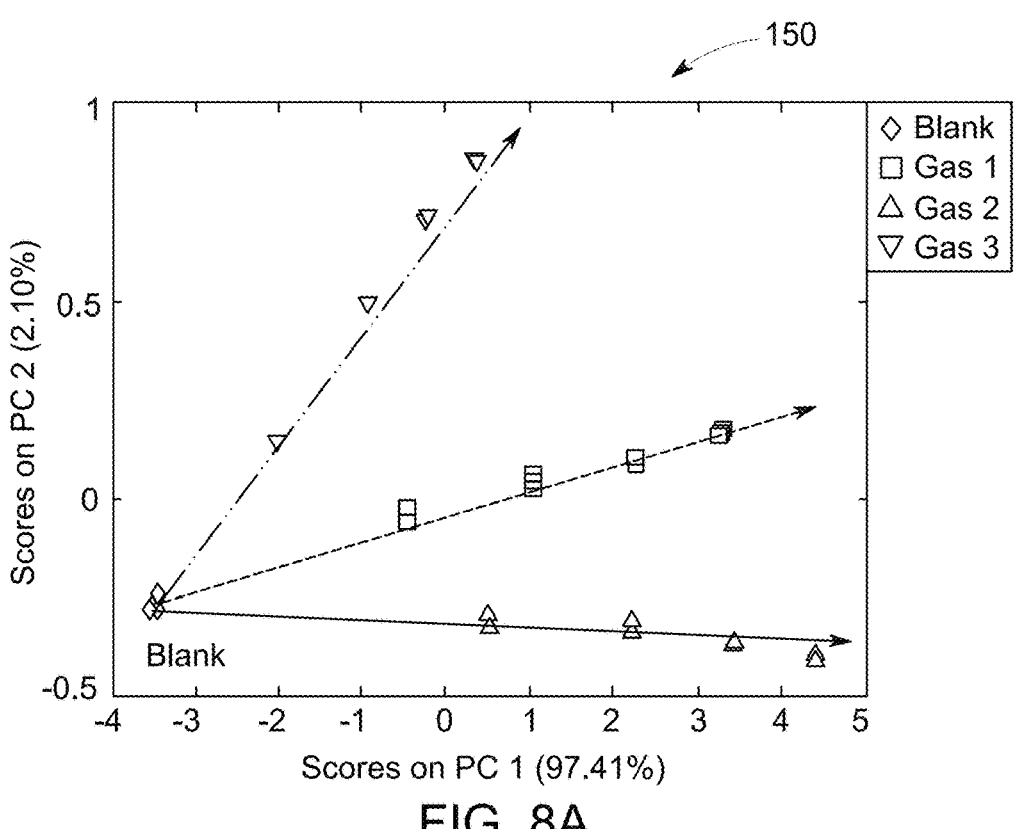
FIG. 8A is a scores plot depicting PCA results of the first two PCs (PC1 versus PC2) of the dielectric excitation responses of the gas sensing material from the second experimental example, in accordance with aspects of the present technique.
Figure 8B:
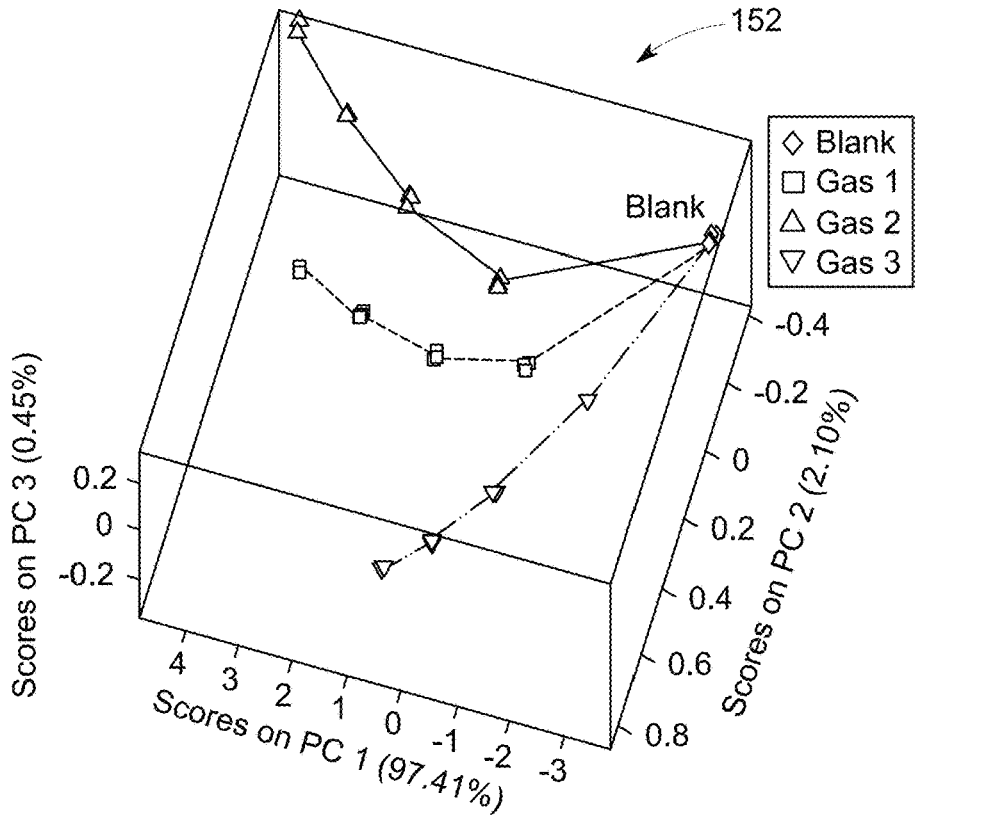
FIG. 8B is a scores plot depicting PCA results as a scores plots of the first three PCs (PC1 versus PC2 versus PC3) of the dielectric excitation responses of the gas sensing material from the second experimental example, in accordance with aspects of the present technique.

For comparison to the resistance measurements and analysis, PCA was also applied to analyze the dielectric excitation responses (e.g., impedance responses) for the second set of experiments to determine the ability of the gas sensor 10 to differentiate between the three analyte gases using the two operating temperatures. FIG. 8A is a scores plot 150 depicting PCA results of the first two PCs (PC1 versus PC2) of the dielectric excitation responses of the gas sensing material 22 when operated at the two operating temperatures, while FIG. 8B is a scores plot 150 depicting PCA results of the first three PCs (PC1 versus PC2 versus PC3) of the dielectric excitation responses of the gas sensing material 22 when operated at the two operating temperatures. In FIGS. 8A and 8B, the scores plots 150 and 152 demonstrate a clear differentiation between the three analyte gases and a high degree of linearity in the correlation between the dielectric excitation responses and the concentrations of the analyte gases. For example, in FIGS. 8A and 8B, the responses for the blank form a tight cluster, and each of the responses for the analyte gases form relatively linear trends that align with the blank samples. As such, unlike the PCA of the DC excitation responses of illustrated in FIGS. 5A and 5B, the scores plots 150, 152 of FIGS. 8A and 8B unexpectedly demonstrate a strong correlation or proportional relationship with a high degree of linearity between the dielectric excitations responses of the gas sensing material 22 and the respective concentrations of the two analyte gases when two operating temperatures are used.

For further comparison between the DC excitation response measurements and the dielectric excitation response measurements, hierarchical cluster analysis (HCA) was also applied to analyze the DC excitation responses (e.g., resistance responses) and the dielectric excitation responses (e.g., impedance responses) for the second set of experiments to determine the ability of the gas sensor 10 to differentiate between the three analyte gases using the two operating temperatures. For the HCA analysis, dendrograms of data with autoscale preprocessing were generated using two PCs for analysis, and K-nearest neighbor algorithm with a Mahalanobis distance metric. The K-nearest neighbor algorithm is a non-parametric method used for classification and regression. Mahalanobis distance is an effective multivariate distance metric that measures the distance between a particular data point and a distribution of data points.

Figure 9:
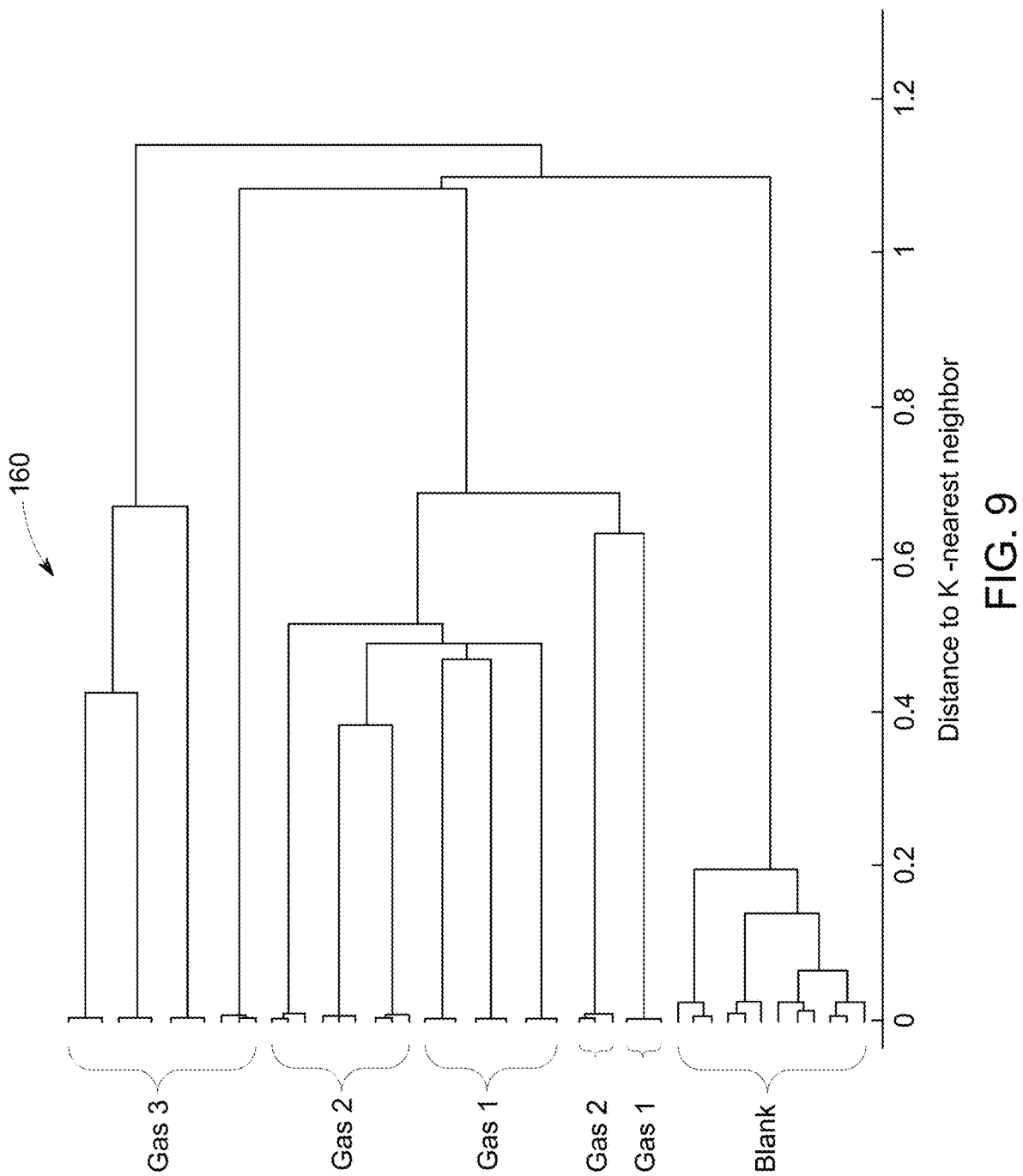
FIG. 9 is a hierarchical cluster analysis (HCA) plot depicting the results of HCA for the logarithmic resistance responses of the gas sensing material from the second experimental example, in accordance with aspects of the present technique.
Figure 10:
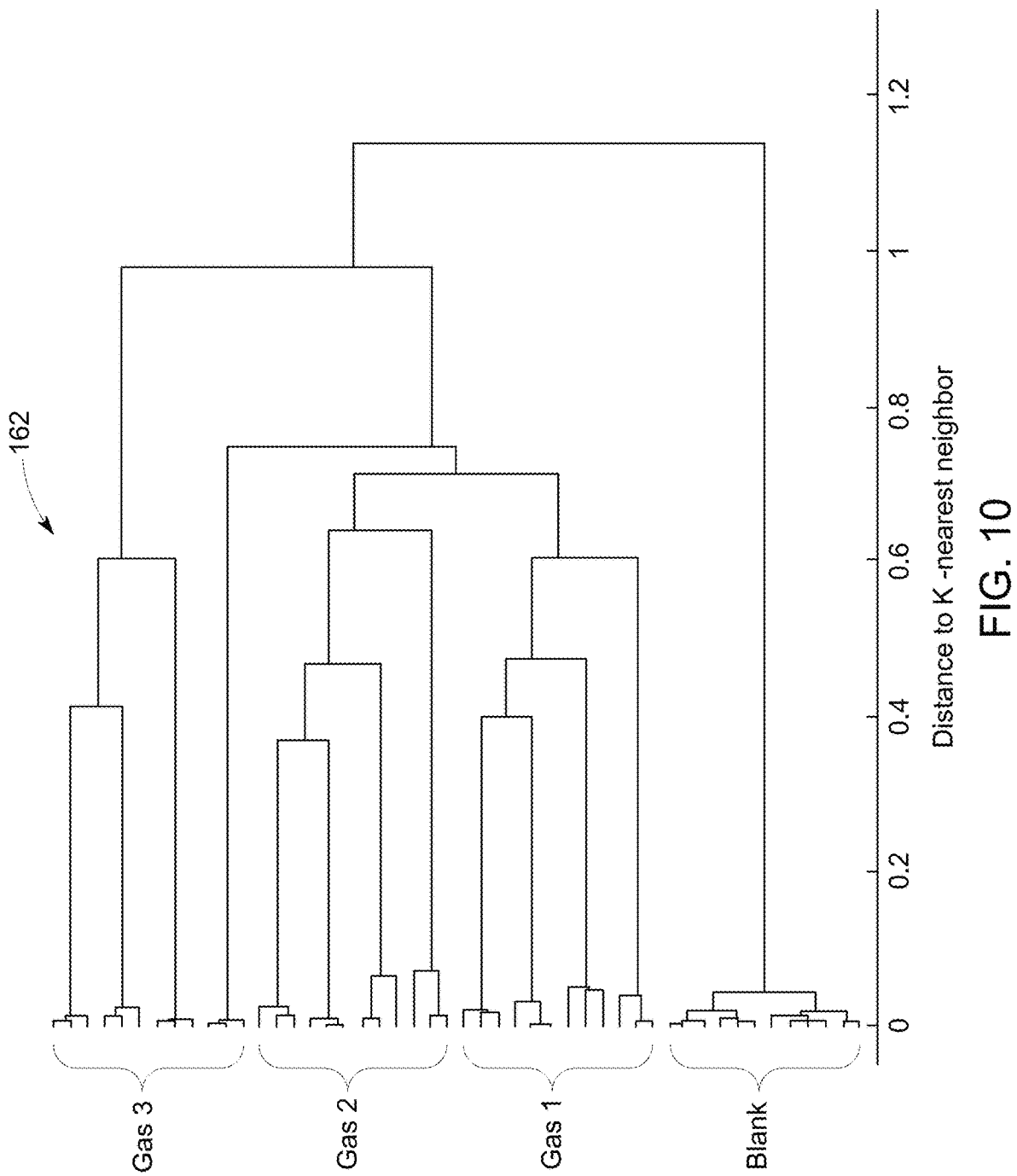
FIG. 10 is a HCA plot depicting the results of HCA for the dielectric excitation responses of the gas sensing material from the second experimental example, in accordance with aspects of the present technique.

FIG. 9 is a HCA plot 160 depicting the results of HCA for the logarithmic resistance responses from the second set of experiments. As illustrated by the HCA plot 160 of FIG. 9, while the blank samples and the third analyte gas are well-resolved from the other analytes, the first and second analyte gases are not well-resolved. For comparison, FIG. 10 is a HCA plot 162 depicting the results of HCA for the dielectric excitation responses from the second set of experiments. As illustrated by the HCA plot 162 of FIG. all three of the analyte gases are desirably resolved from each other, as well as from the blank samples.

Experimental Example 3

To further demonstrate the superior performance of the disclosed technique, a third set of experiments was also performed to compare the ability of conventional resistance measurements versus dielectric excitation measurements for the differentiation between three different analyte gases in fluid samples at three operating temperatures. For the third set of experiments, all measurements were performed using a metal-salt-doped tin oxide ($SnO_2$) as the gas sensing material 22. The measurements were performed by the measurement circuit 32 as either DC excitation responses (e.g., resistance measurements), or as dielectric excitation responses (e.g., impedance measurements) selected from the high-frequency shoulder region 106 or 108 of corresponding impedance spectrum 100 after dielectric excitation. Each excitation response measurement was performed with a heating element voltage of 5 V (corresponding to a first operating temperature), and also performed with a heating element voltage of 6 V (corresponding to a second operating temperature), and also performed with a heating element voltage of 7 V (corresponding to a second operating temperature). For the embodiment of the gas sensor 10 used for these experiments, the 5 V heating element voltage corresponds to an operating temperature of approximately 200 degrees Celsius (° C.), the 6 V heating element voltage corresponds to an operating temperature of approximately 230° C., and, the 7 V heating element voltage corresponds to an operating temperature of approximately 265° C.

For the third set of experiments, the gas sensor 10 was exposed to each three different analyte gases at three different concentrations. The first analyte gas was toluene vapor, and the three different concentrations of the first analyte gas were: 6.25 ppm, 12.5 ppm, and 18.75 ppm. The second analyte gas was acetone vapor, and the three different concentrations of the second analyte gas were: 6.25 ppm, 12.5 ppm, and 18.75 ppm. The third analyte gas was benzene vapor, and the three different concentrations of the third analyte gas were: 6.25 ppm, 12.5 ppm, and 18.75 ppm. As such, for the third set of experiments, the gas sensor 10 was: (A) heated to the first operating temperature, (B) exposed to a blank sample while resistance responses and impedance responses were measured, (C) exposed to each of the three concentrations of the first analyte gas while resistance responses and impedance responses were measured, (D) exposed to each of the three concentrations of the second analyte gas while resistance responses and impedance responses were measured, (E) exposed to each of the three concentrations of the third analyte gas while resistance responses and impedance responses were measured, and then (F) exposed to a blank sample while resistance responses and impedance responses were measured. The gas sensor 10 was then heated to the second operating temperature while steps (B)-(F) were repeated, and then the gas sensor 10 was then heated to the third operating temperature while steps (B)-(F) were repeated once again. For each sensor state (different concentrations of two analyte gases and a blank), three data points were extracted from the raw dynamic response at the steady-state or maximum signal change of the sensor response.

Figures 11A, 11B, 11C:
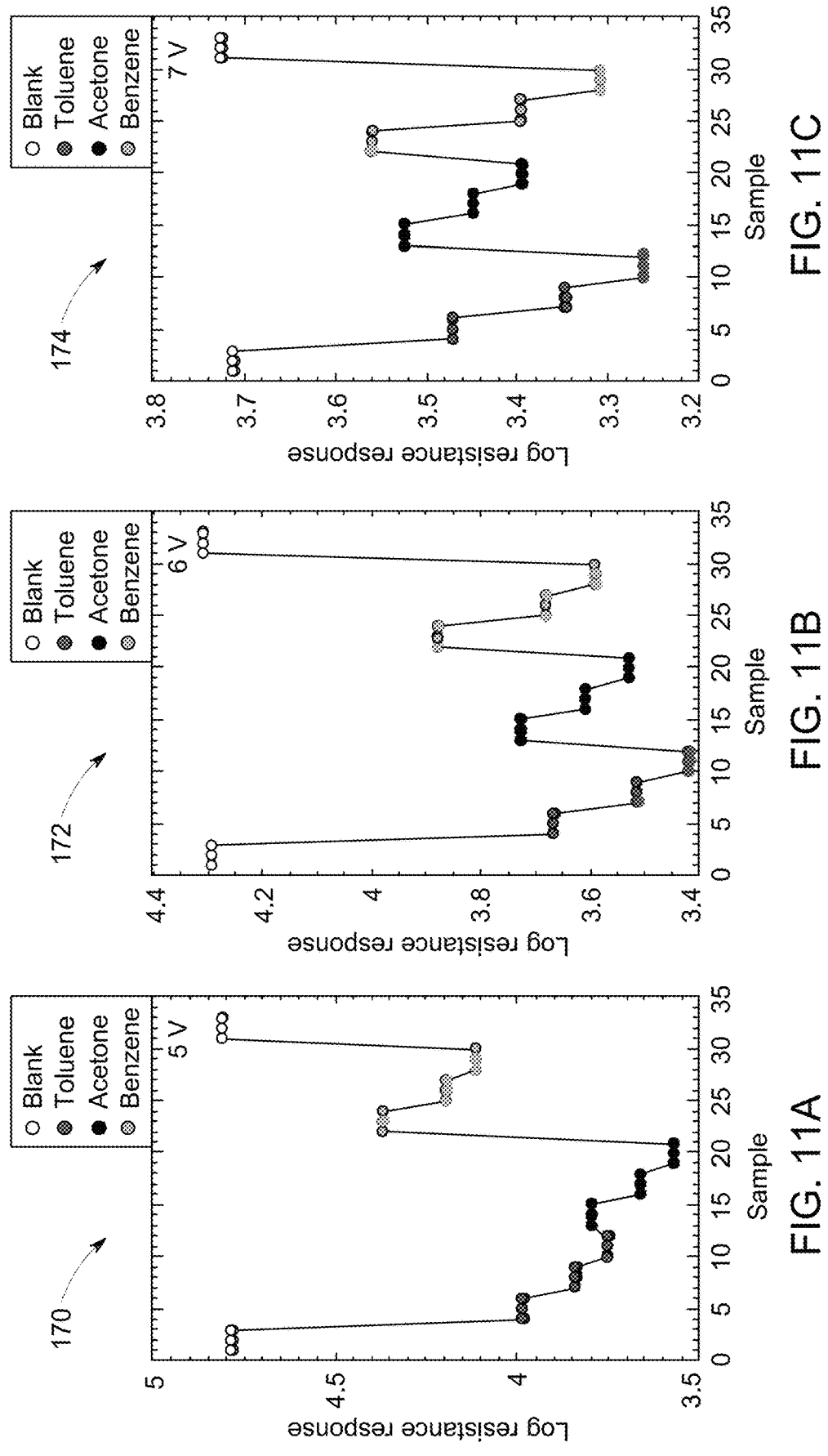
FIGS. 11A, 11B, and 11C depict the logarithmic resistance responses of the gas sensing material from the third experimental example, in accordance with aspects of the present technique.

FIGS. 11A-C depict the logarithmic resistance responses of the gas sensor 10 for the third set of experiments. More specifically, FIG. 11A is a graph 170 illustrating the logarithmic resistance responses of the gas sensor 10 at the first operating temperature, FIG. 11B is a graph 172 illustrating the logarithmic resistance responses of the gas sensor at the second operating temperature, and FIG. 11C is a graph 174 illustrating the logarithmic resistance responses of the gas sensor 10 at the third operating temperature. The logarithmic resistance responses of FIGS. 11A-C indicate that the logarithmic resistance responses have a particular pattern at different operating temperatures. For the illustrated example, the magnitudes of the logarithmic resistance responses from the smallest to the largest are: at a 5 V heating element voltage (first operating temperature), the pattern is the third analyte gas (benzene), followed by the first analyte gas (toluene), followed by the second analyte gas (acetone); at a 6 V heating element voltage (second operating temperature), the pattern is the third analyte gas (benzene), followed by the second analyte gas (acetone), followed by the first analyte gas (toluene); and at a 7 V heating element voltage (third operating temperature), the pattern is the second analyte gas (acetone), followed by third analyte gas (benzene), followed by the first analyte gas (toluene). However, even using the logarithmic scale, the resistance responses are nonlinear. It may be appreciated that such non-linearity significantly reduces the ability for the differentiation and quantitation of different analytes. In addition, it is presently recognized that such non-linearity imposes a significant and undesirable burden for calibration of the gas sensor 10.

Figure 12A:
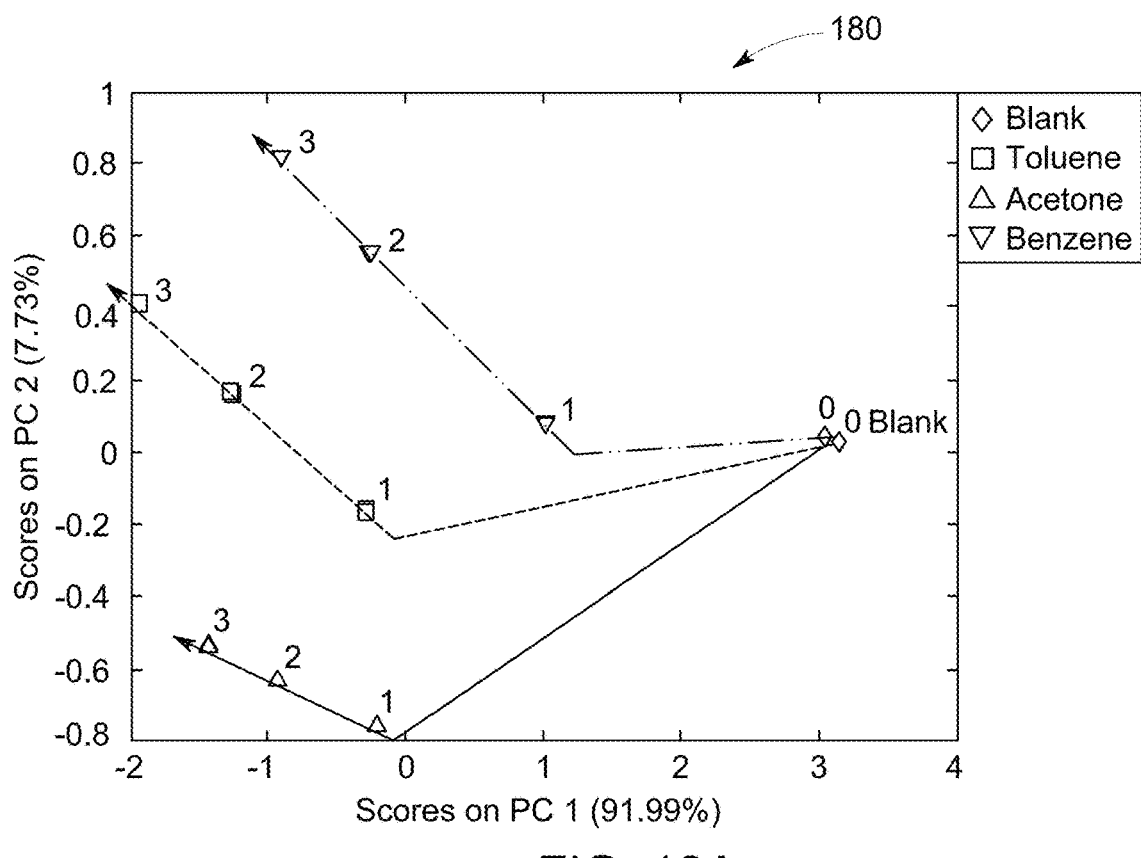
FIG. 12A is a scores plot depicting the first two principal components (PC1 versus PC2) from the PCA analysis of the logarithmic resistance responses of the gas sensing material from the third experimental example, in accordance with aspects of the present technique.
Figure 12B:
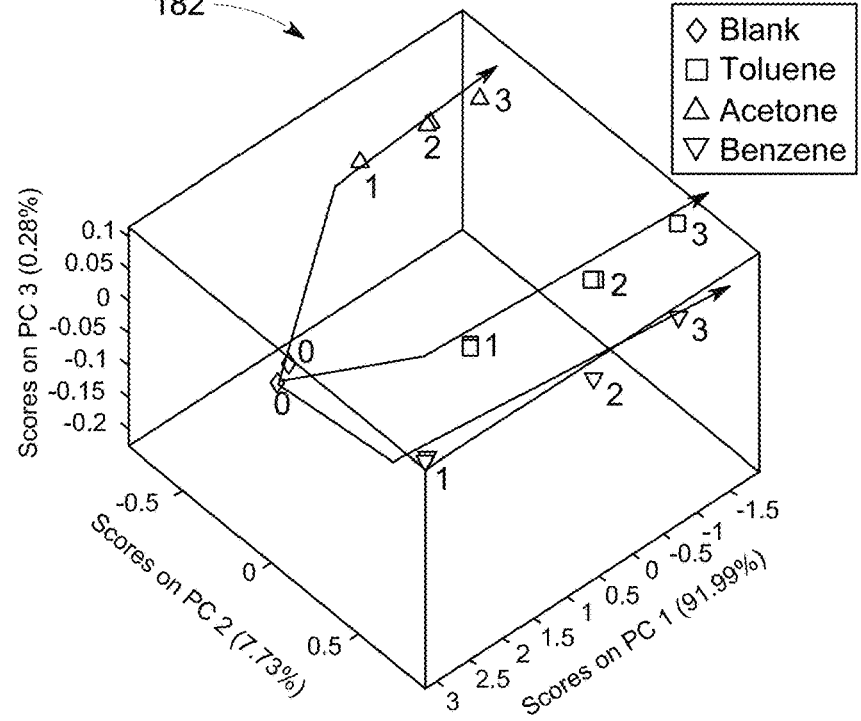
FIG. 12B is a scores plot depicts the first three principal components (PC1 versus PC2 versus PC3) from the PCA analysis of the logarithmic resistance responses of the gas sensing material from the third experimental example, in accordance with aspects of the present technique.
Figure 13A:
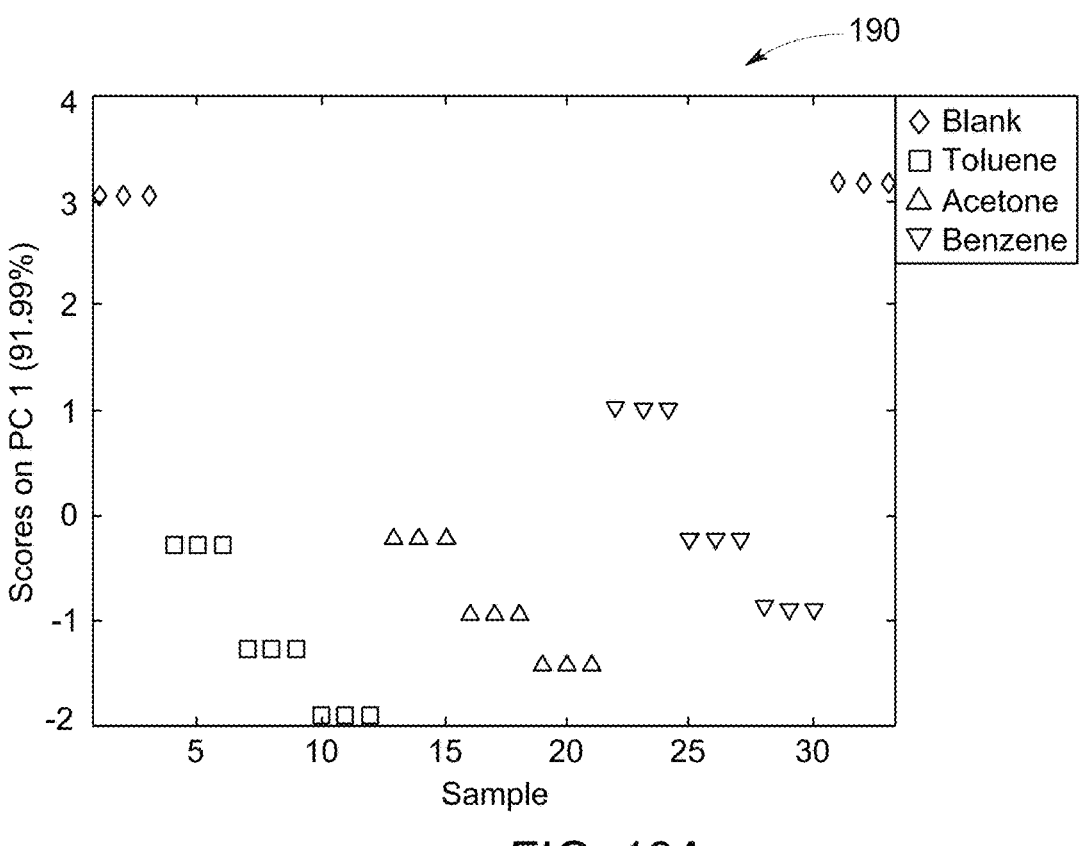
FIGS. 13A, 13B, and 13C are graphs illustrating contributions of each of PC1, PC2, and PC3 into the response pattern of the gas sensing material with resistance readout from the third experimental example, in accordance with aspects of the present technique.
Figure 13B:
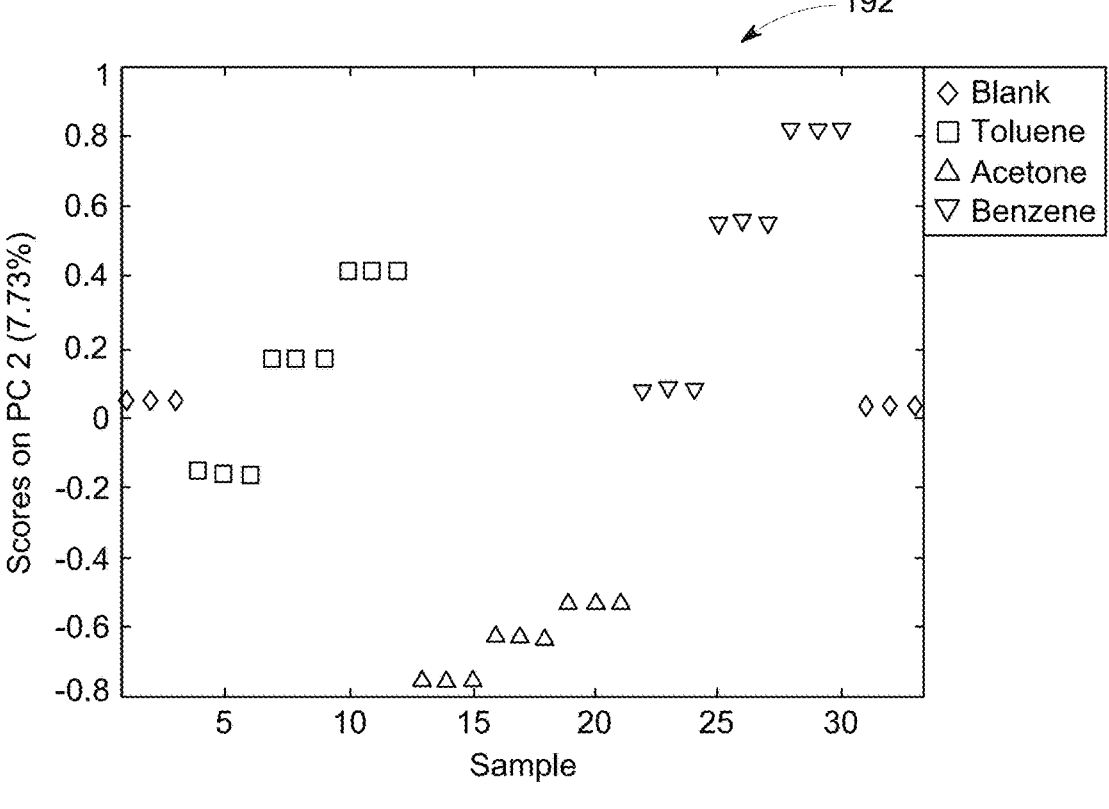
Figure 13C:
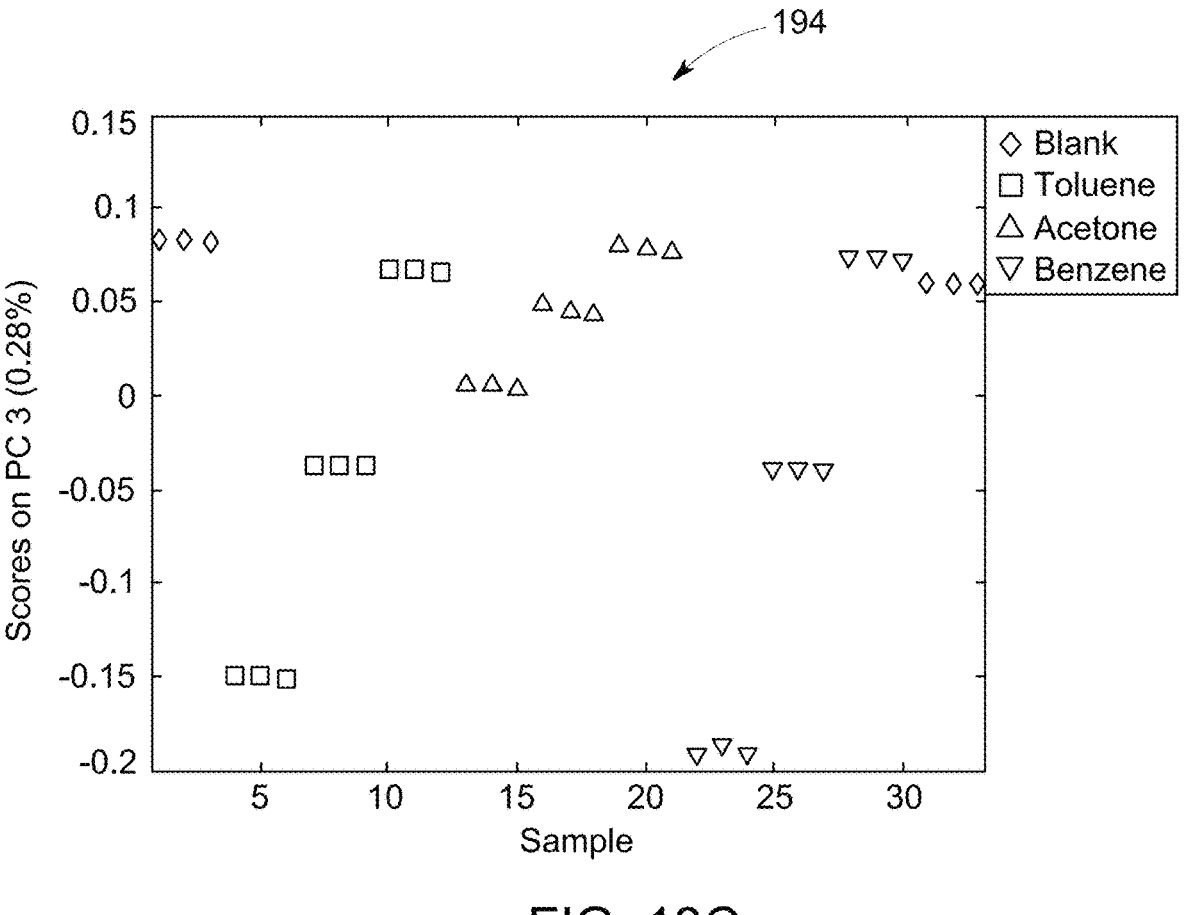

PCA was applied to analyze resistance responses (e.g., DC excitation responses) for the third set of experiments to determine the ability of the gas sensor 10 to differentiate between the three analyte gases using the three operating temperatures. FIG. 12A is a scores plot 180 depicting the results of PCA for the first two principal components (PC1 versus PC2) in the analysis of the logarithmic resistance responses, while FIG. 12B is a scores plot 182 depicting the results of PCA for the first three principal components (PC1 versus PC2 versus PC3) in the analysis of the logarithmic resistance responses. Both FIGS. 12A and 12B demonstrate desirable differentiation between the three analyte gases; however, both plots also demonstrate significant and undesirable gas-response non-linearity and non-monotonic behavior. FIGS. 13A-C illustrate contributions of each of PC1, PC2, and PC3 into the response pattern of the gas sensor 10 with the resistance readout.

For example, as illustrated by the plot 190 of FIG. 13A, the resistance responses of the gas sensor 10 track with the concentrations of three vapors monotonically only for PC1. In the plot 192 of FIG. 13B, resistance responses to the first analyte gas (toluene) and the second analyte gas (acetone) are non-monotonic, while only the resistance responses to the third analyte gas (benzene) are monotonic in PC2. In the plot 194 of FIG. 13C, responses to all three analytes are non-monotonic for PC3. It is presently recognized that such non-monotonic responses of the gas sensor 10 significantly reduces the accuracy of differentiation between analytes, and accuracy of the quantitation of different analytes, and the ability for the quantitation of different mixtures of analytes.

Figures 14A, 14B, 14C:
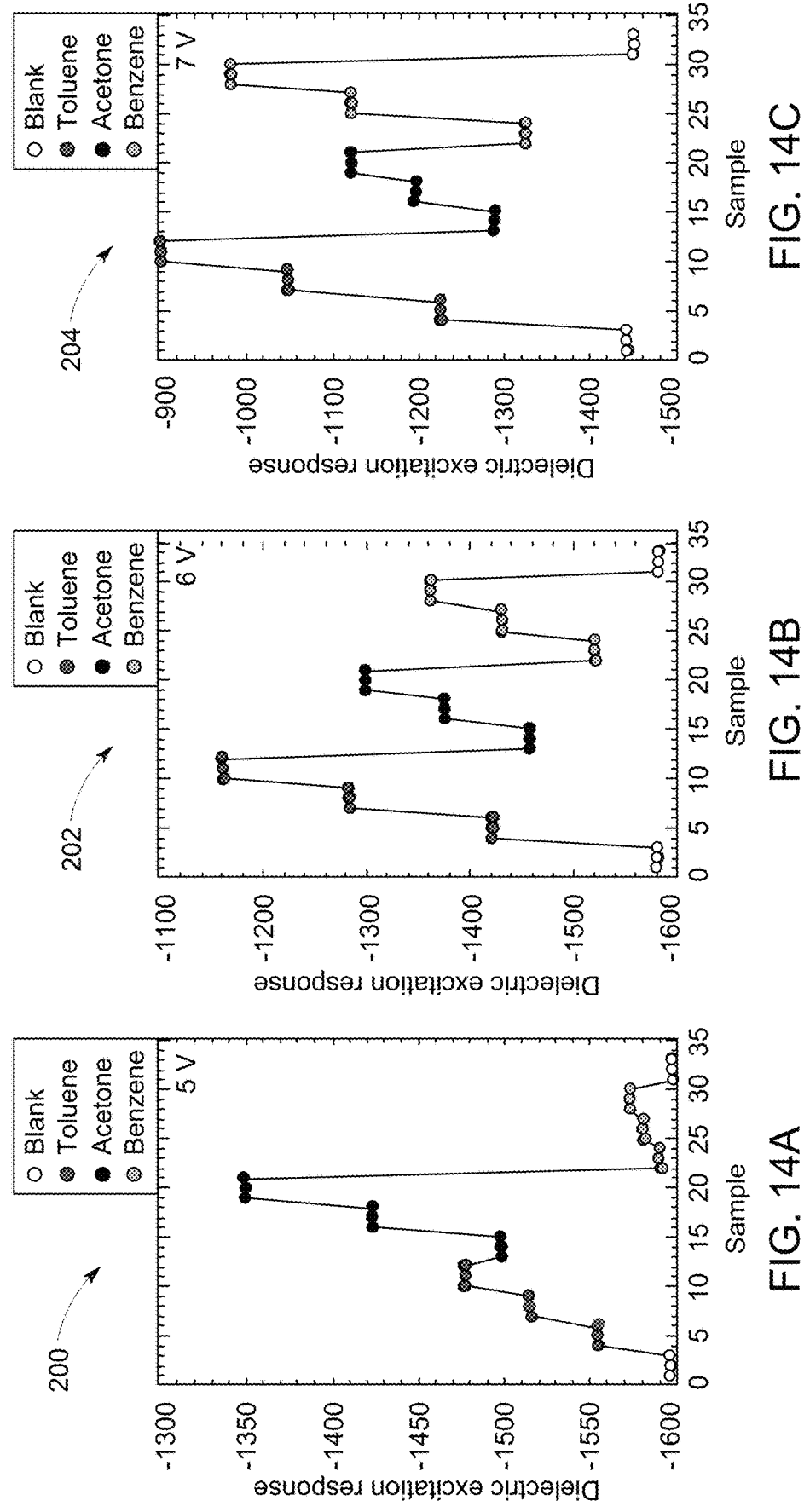
FIGS. 14A, 14B, and 14C are graphs depicting the dielectric excitation responses of the gas sensing material for the third experimental example, in accordance with aspects of the present technique.

FIGS. 14A-C depict the dielectric excitation responses of the gas sensor 10 for the third set of experiments. More specifically, the graph 200 of FIG. 14A illustrates the dielectric excitation responses of the gas sensor 10 at the first operating temperature, the graph 202 of FIG. 14B illustrates the dielectric excitation responses of the gas sensor 10 at the second operating temperature, and the graph 204 of FIG. 14C illustrates the dielectric excitation responses of the gas sensor 10 at the third operating temperature. The dielectric excitation responses of FIGS. 14A-C have a particular pattern at the different operating temperatures. For the illustrated example, the magnitudes of the dielectric excitation responses from the smallest to the largest are: at a 5 V heating element voltage (first operating temperature), the pattern is the third analyte gas (benzene), followed by the first analyte gas (toluene), followed by the second analyte gas (acetone); at a 6 V heating element voltage (second operating temperature), the pattern is the third analyte gas (benzene), followed by the second analyte gas (acetone), followed by the first analyte gas (toluene); and at a 7 V heating element voltage (third operating temperature), the pattern is the second analyte gas (acetone), followed by third analyte gas (benzene), followed by the first analyte gas (toluene). As such, for the embodiment of the gas sensor 10 used for the third set of experiments, this pattern for dielectric excitation response magnitude at different operating temperatures matches the pattern for the DC excitation responses. However, unlike the resistance responses of FIGS. 11A-C, the dielectric excitation responses of FIGS. 14A-C have a high degree of linearity or are entirely linear. It is presently recognized that this high degree of linearity significantly improves the ability of the gas sensor 10 to differentiate between different analytes and to quantify concentrations of different analytes. Additionally, this high degree of linearity reduces the burden for calibration of the gas sensor 10.

Response linearity of the gas sensor 10 when measured with logarithmic resistance response (e.g., FIGS. 11A-C) or dielectric excitation response (e.g., FIGS. 14A-C) was determined as the coefficient of determination $R^2$ of the linear fit between the gas concentrations and sensor response. For the logarithmic resistance responses at three voltages of 5V, 6V, and 7V: $R^2$ for the first analyte gas was 0.787, 0.829, and 0.945, respectively; $R^2$ for the second analyte gas was 0.751, 0.811, and 0.913, respectively; and $R^2$ for the third analyte gas was 0.891, 0.907, and 0.985, respectively. For the dielectric excitation responses at three voltages of 5V, 6V, and 7 V: $R^2$ for the first analyte gas was 0.996, and 0.992, respectively; $R^2$ for the second analyte gas was 0.994, 0.986, and respectively; and $R^2$ for the third analyte gas was 0.993, 0.994, and 0.991, respectively. Thus, response linearity of the gas sensor 10 was consistently higher when measured as the dielectric excitation response (e.g., FIGS. 14A-C) as compared to the response linearity of the gas sensor 10 when measured as the logarithmic resistance response (e.g., FIGS. 11A-C).

Figure 15A:
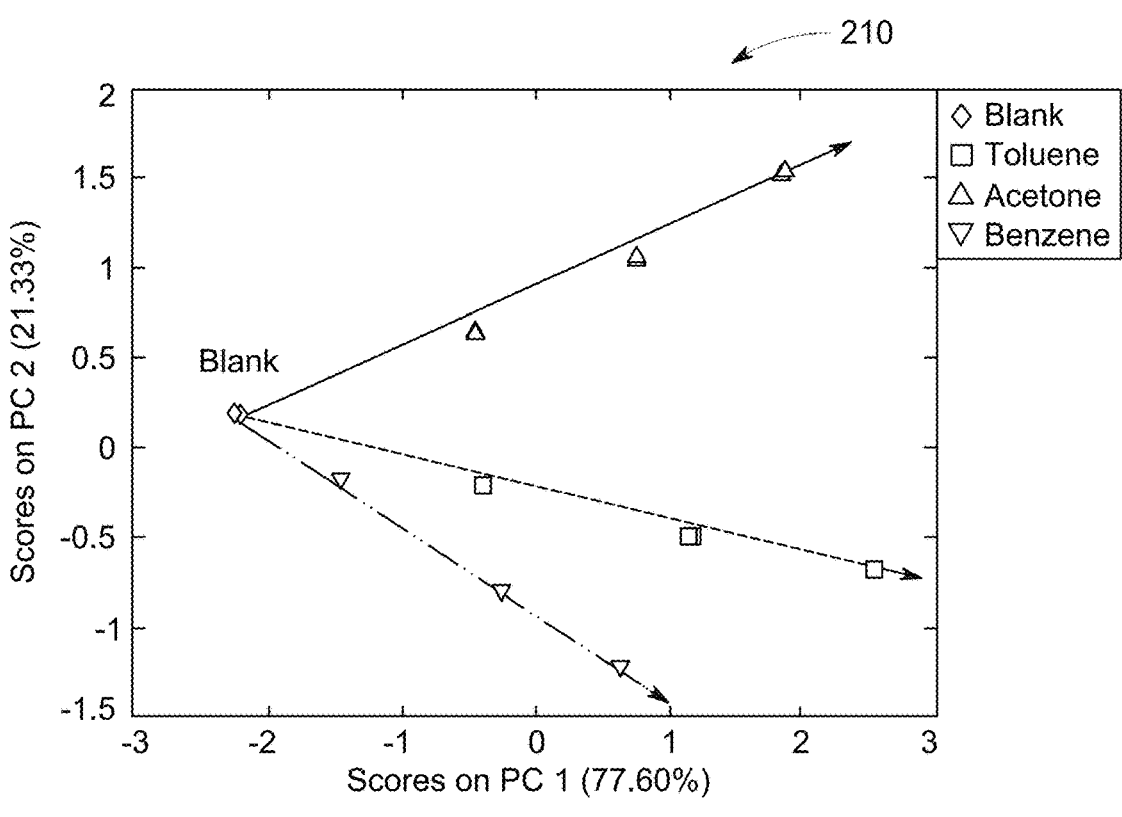
FIG. 15A is a scores plot depicting the first two principal components (PC1 versus PC2) from the PCA analysis of the dielectric excitation responses of the of the gas sensing material for the third experimental example, in accordance with aspects of the present technique.
Figure 15B:
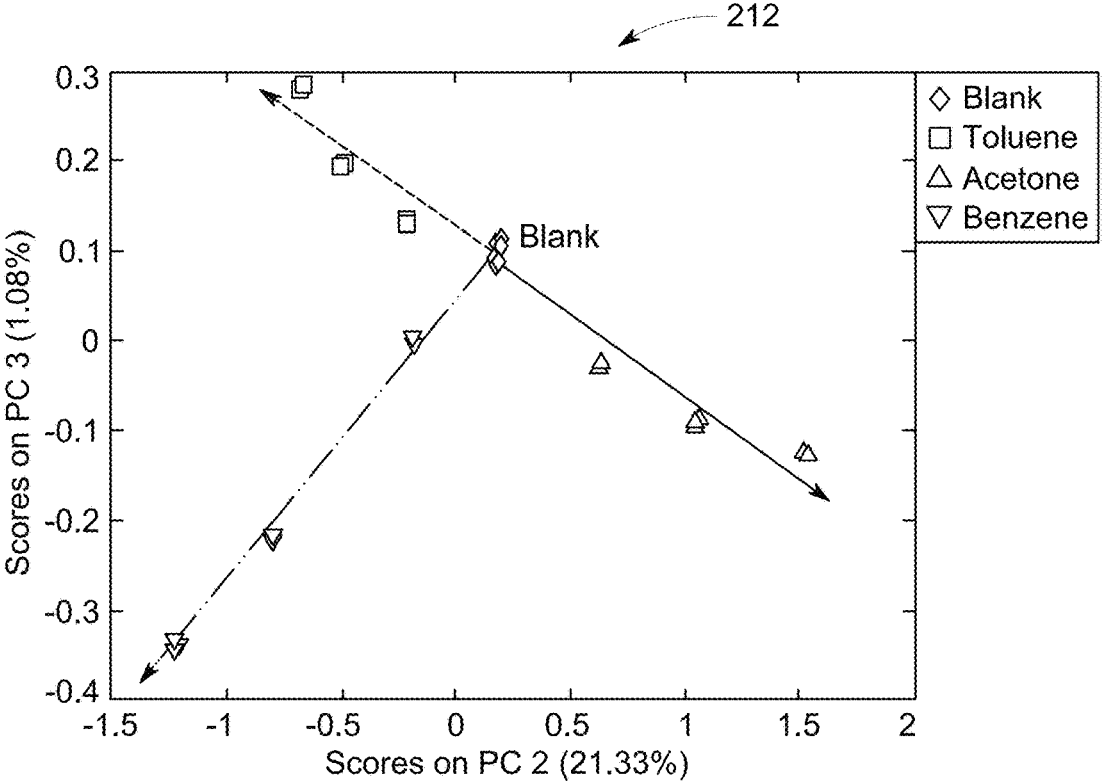
FIG. 15B is a scores plot depicting the second and third principal components (PC2 versus PC3) from the PCA analysis of the dielectric excitation responses of the of the gas sensing material for the third experimental example, in accordance with aspects of the present technique.
Figure 15C:
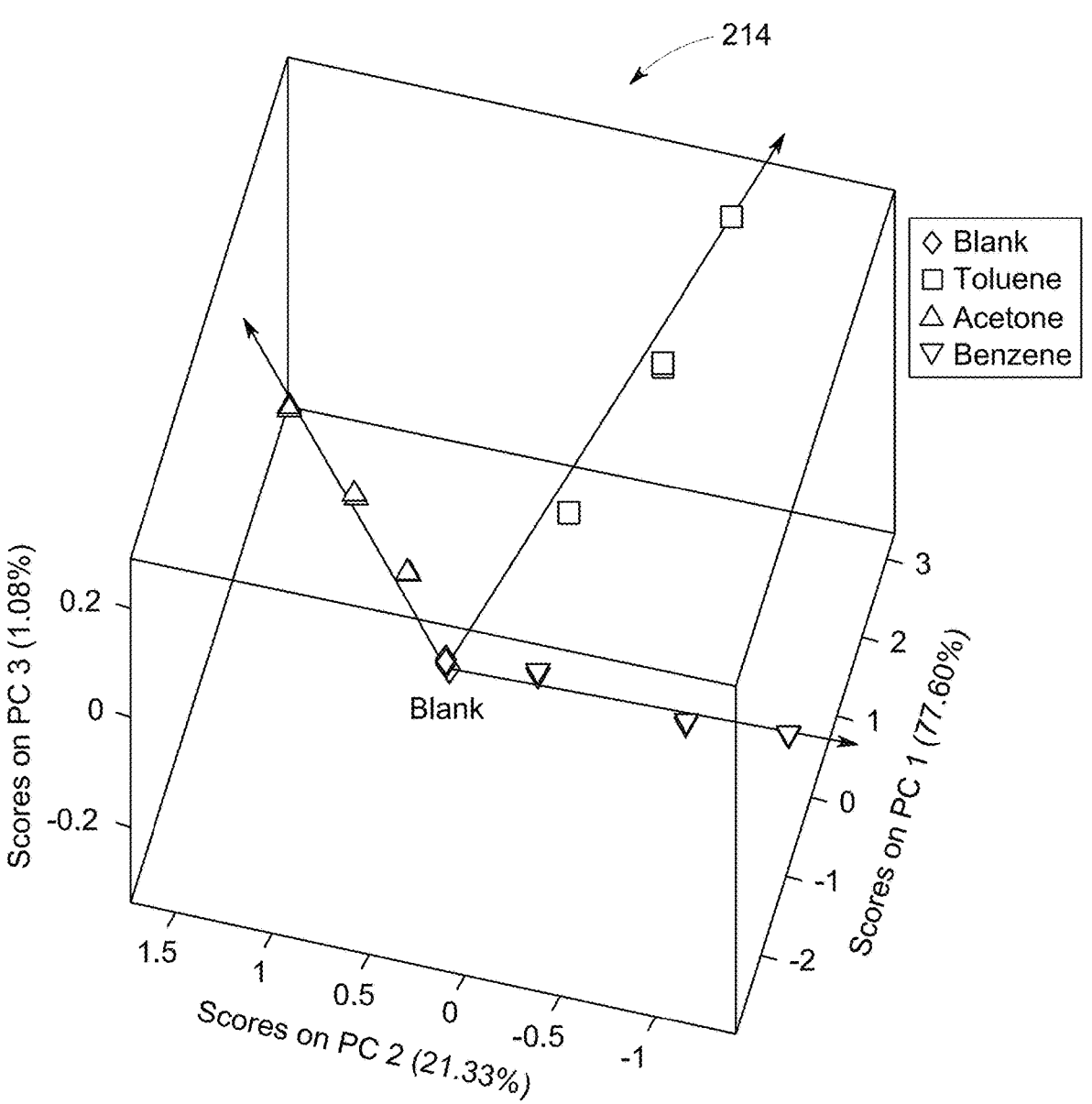
FIG. 15C is a scores plot depicting the first three principal components (PC1 versus PC2 versus PC3) from the PCA analysis of the dielectric excitation responses of the of the gas sensing material for the third experimental example, in accordance with aspects of the present technique.
Figure 16A:
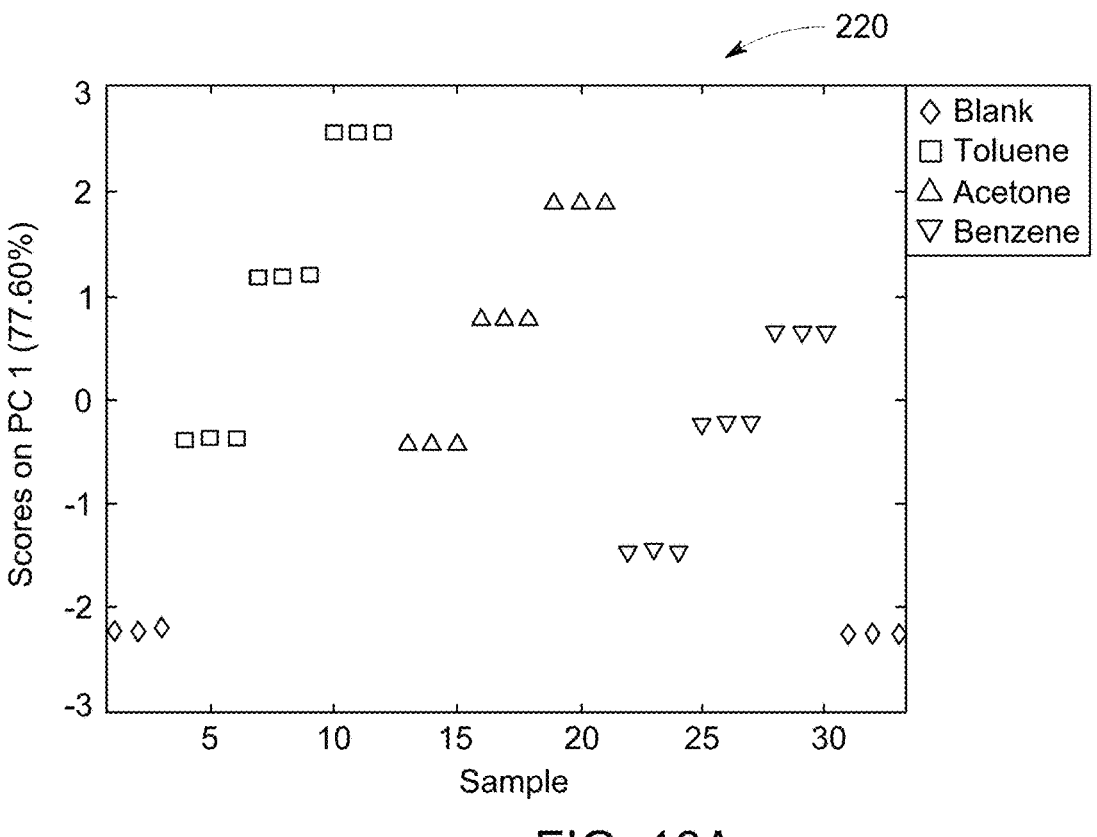
FIGS. 16A, 16B, and 16C are a set of graphs illustrating contributions of each of PC1, PC2, and PC3 into the response pattern of the of the gas sensing material with the dielectric excitation readout for the third experimental example, in accordance with aspects of the present technique.
Figure 16B:
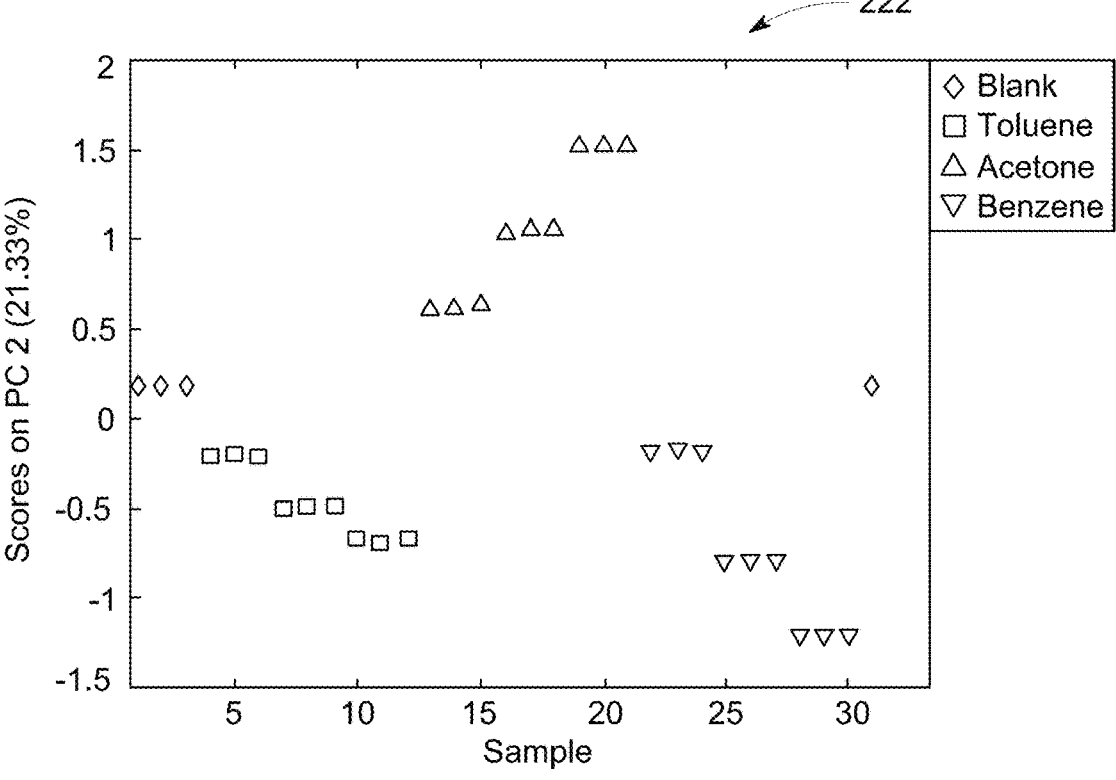
Figure 16C:
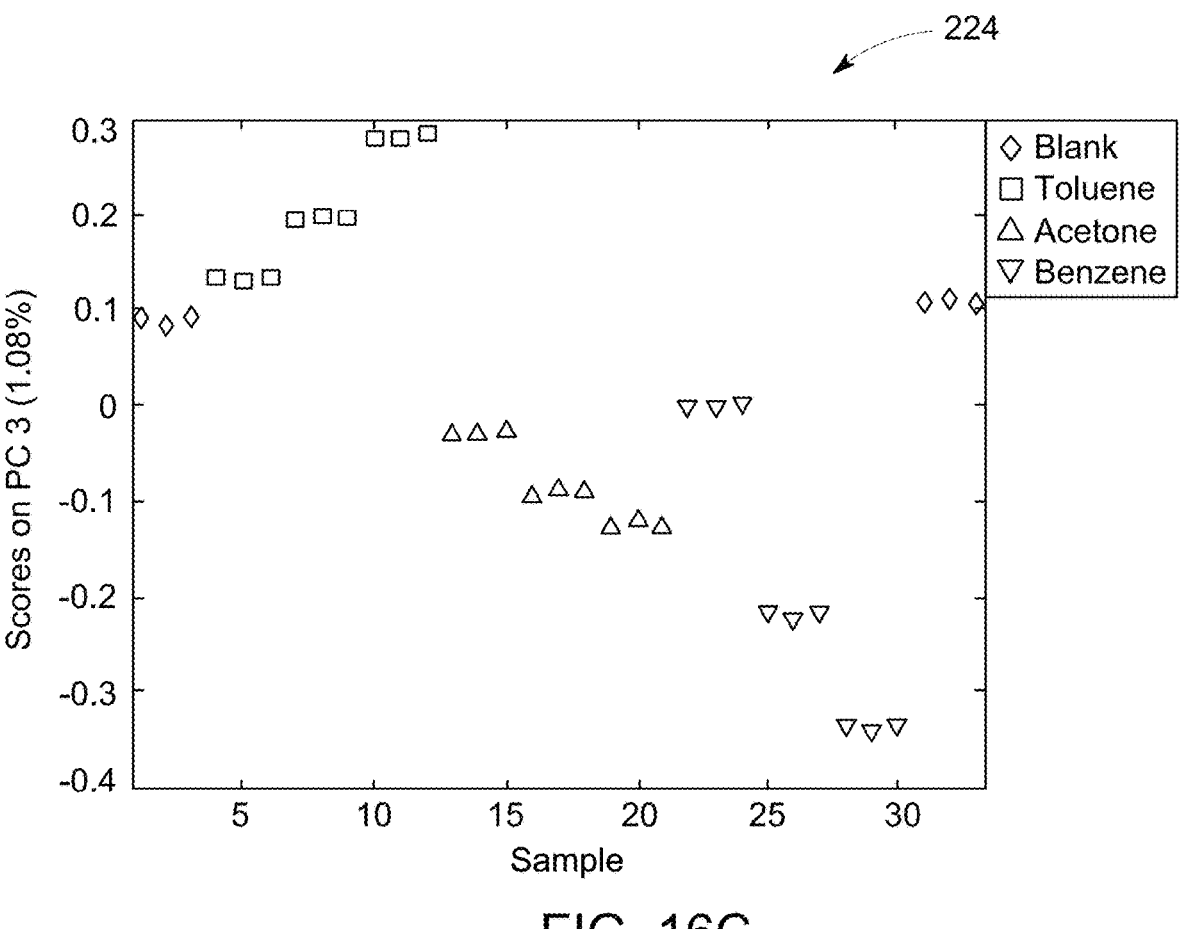

PCA was applied to analyze dielectric excitation responses for the third set of experiments to determine the ability of the gas sensor 10 to differentiate between the three analyte gases using the three operating temperatures. FIG. 15A is a scores plot 210 depicting the results of PCA for the first two principal components (PC1 versus PC2) in the analysis of the dielectric excitation responses, FIG. 15B is a scores plot 212 depicting the results of PCA for the second and third principal components (PC2 versus PC3) in the analysis of the dielectric excitation responses, while FIG. 15C is a scores plot 214 depicting the results of PCA for the first three principal components (PC1 versus PC2 versus PC3) in the analysis of the dielectric excitation responses. All of the scores plots of FIGS. 15A-C demonstrate differentiation between the three analyte gases with a high degree of response linearity. FIGS. 16A-C illustrate contributions of each of PC1, PC2, and PC3 into the response pattern of the gas sensor 10 with the dielectric excitation readout (responses). In each of the plots 220, 222, and 224 of FIGS. 16A-C, the responses of the gas sensor 10 desirably track with the concentrations of three analytes linearly and monotonically for all three PCs. Such monotonic behavior of the gas sensor 10 facilitates accurate differentiation between analytes, facilitates accurate quantitation of different analytes, and the ability for the quantitation of different analyte mixtures.

A comparison was further performed of the multi-gas differentiation and linearity that can be achieved with fewer operating temperatures if using dielectric excitation responses versus resistance responses with the same MOS gas sensing material. In FIG. 12A and FIG. 12B resistance responses were analyzed by applying PCA to determine the ability of the gas sensor 10 to differentiate between the three analyte gases using resistance responses and the three operating temperatures related to 5 V, 6 V, and 7 V of the heating element voltages. The contributions of PC1, PC2, and PC3 were 91.99%, 7.73%, and respectively, corresponding to the 100% of variation captured by three PCs. The more contributions are in the higher PCs, the stronger the sensor dispersion is. Sensor response dispersion or dimensionality is the sensor ability to provide independent outputs generated by the sensor. FIGS. 12A and 12B demonstrate that three gases were differentiated but with two important points. First, the non-linear responses for all three gases were observed. Second, the contribution to PC1 of 91.99% was relatively large and did not leave much for the other PCs to support a 2D or 3D dispersion of the gas sensor response when operated at three temperatures.

Figure 17:
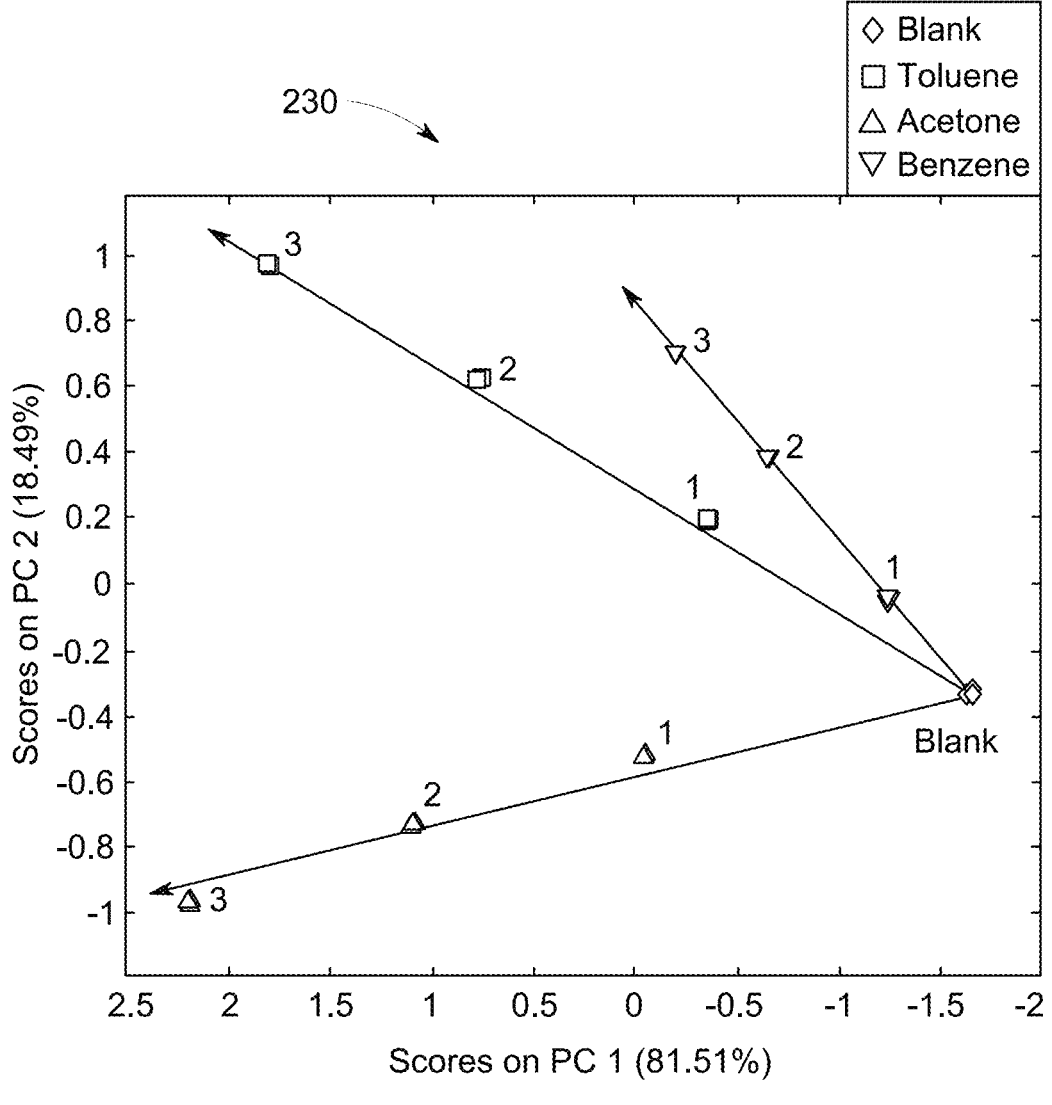
FIG. 17 is a scores plot depicting the first two principal components (PC1 versus PC2) from the PCA analysis of the dielectric excitation responses of the gas sensing material for the third experimental example at two operating temperatures, in accordance with aspects of the present technique.

In contrast, using dielectric excitation responses for the third set of experiments, only two operating temperatures were used to determine the ability of the gas sensor 10 to differentiate between the three analyte gases. The two operating temperatures were related to 5 V and 6 V of the heating element voltages. FIG. 17 is a scores plot 230 depicting the results of PCA for the first two principal components (PC1 versus PC2) in the analysis of the dielectric excitation responses. The contribution PC1 was 81.51% and the contribution PC2 was 18.49% corresponding to the 100% of variation captured by the two PCs. FIG. 17 demonstrated that three gases were differentiated with three important points. First, the linear responses for all three gases were observed. Second, the contribution to PC1 of 81.51% allowed a substantial value for PC2, which was 18.49%. Third, the contribution PC2 of 18.49% by the dielectric excitation response of the MOS gas sensor was 2.4-fold stronger as compared to the contribution PC2 of 7.73% by the resistance response obtained even with more levels of operating temperatures. Such larger value of PC2 achieved with the dielectric excitation responses is important for multi-gas differentiation.

Figure 18A:
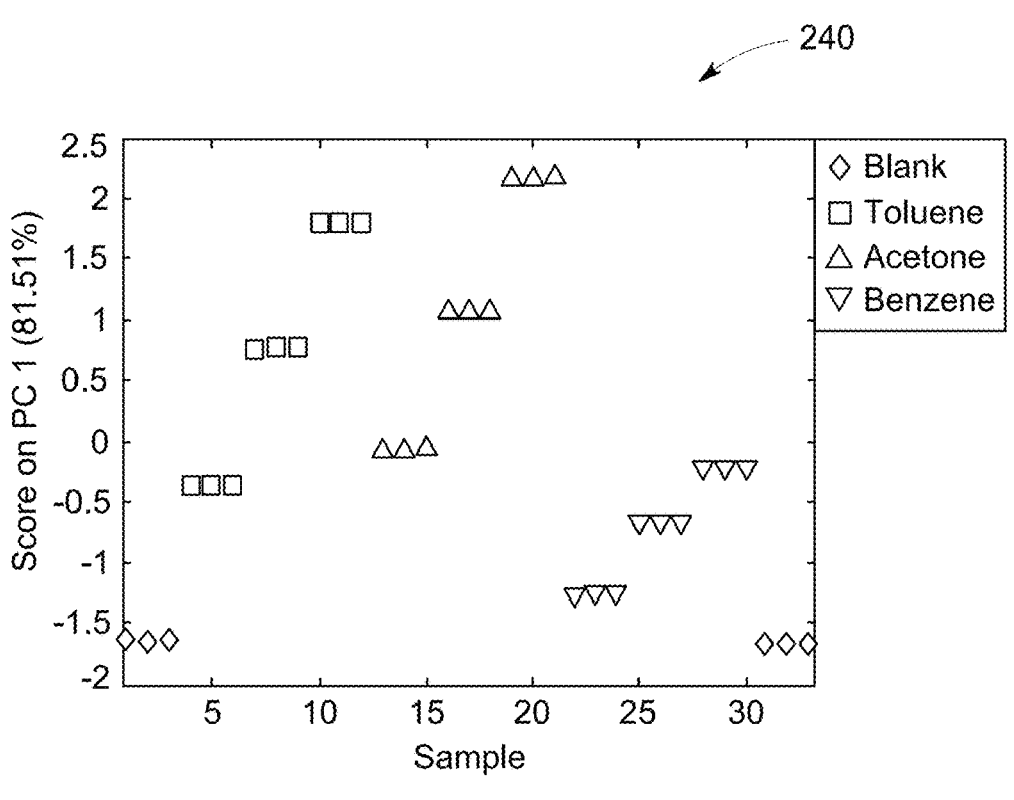
FIGS. 18A and 18B are a set of graphs illustrating contributions of each of PC1 and PC2 into the response pattern of the of the gas sensing material with the dielectric excitation readout for the third experimental example at the two operating temperatures, in accordance with aspects of the present technique.
Figure 18B:
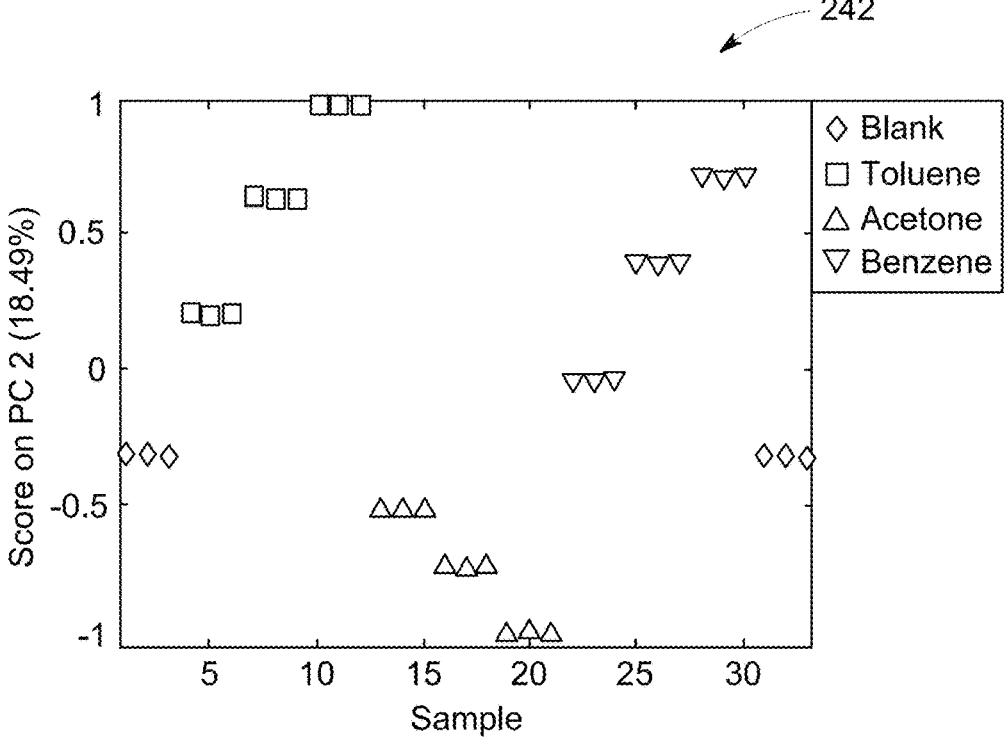

FIGS. 18A and 18B illustrate contributions of each of PC1 and PC2 into the response pattern of the gas sensor 10 with the dielectric excitation responses and two operating temperatures. In each of the plots 240 and 242 of FIGS. 18A and 18B, the responses of the gas sensor 10 desirably track with the concentrations of three analytes linearly and monotonically for all two PCs. Such monotonic and linear behavior of the gas sensor 10 facilitates accurate differentiation between analytes, facilitates accurate quantitation of different analytes, and the ability for the quantitation of different analytes in mixtures.

In contrast, FIGS. 13A-C illustrate contributions of each of PC1, PC2, and PC3 into the response pattern of the gas sensor 10 with the resistance responses at three operating temperatures. The resistance responses of the gas sensor 10 track with the concentrations of three vapors monotonically only for PC1 as depicted by the plot 190 of FIG. 13A. Such monotonic responses to vapors progressively degrade into non-monotonic responses for higher PCs. In the plot 192 for PC2 of FIG. 13B, resistance responses to the first and the second analyte gases are non-monotonic, while only the resistance responses to the third analyte gas are monotonic. In the plot 194 of FIG. 13C, responses to all three analytes are non-monotonic for PC3. Thus, by measuring dielectric excitation responses of the gas sensing material, enhanced multi-gas differentiation can be achieved using fewer operating temperatures than would be used by the same MOS gas sensing material configured to perform multi-gas differentiation based on resistance responses alone.

Technical effects of the invention include enabling multi-gas sensing using a fewer number of temperature cycles, as compared to traditional resistance-based gas sensing. That is, by measuring dielectric excitation responses of the gas sensing material, enhanced multi-gas differentiation and resolution can be achieved using fewer operating temperatures than would be used by the same MOS gas sensing material configured to perform multi-gas differentiation based on resistance responses alone. Additionally, the disclosed gas sensors and gas sensing techniques enable improved response linearity, improved dynamic range, and reduced computational resource consumption for multi-gas quantitation relative to traditional resistance-based gas sensing methods. Furthermore, by reducing the number of operating temperature switching events, present embodiments enable gas sensors with improved measurement quality and enhanced operational lifetimes. That is, using a set of predetermined operating temperatures, the dielectric relaxation spectrum of a gas sensing material is differently affected by different gases, and such desired differences are more pronounced as compared to the resistance response of the same gas sensing material, even when additional operating temperatures are used. Thus, present embodiments unexpectedly demonstrate MOS-based gas sensors that can differentiate between different gases using responses collected using at least two different operating temperatures, wherein this differentiation is superior in the differentiation between different gases and in baseline stability, as compared to the resistance response of the same gas sensing material at more than two operating temperatures.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A gas sensor system for multi-gas analysis of a fluid sample, comprising:
   a gas sensing element configured to operate at multiple temperatures and to contact the fluid sample;
   a heating element coupled to the gas sensing element and configured to heat the gas sensing element;
   a heater controller operatively coupled to the heating element and configured to control the heating element to heat the gas sensing element to each of the multiple temperatures while the gas sensing element contacts the fluid sample;
   a measurement circuit operatively coupled to the gas sensing element and configured to provide dielectric excitation to, and to measure dielectric excitation responses of, the gas sensing element while the gas sensing element is heated to each of the multiple temperatures and contacts the fluid sample, wherein the measured dielectric excitation responses provide enhanced differentiation between at least two gases and improved response linearity to the at least two gases in the fluid sample as compared to resistance responses of the gas sensing element when contacting the fluid sample at each of the multiple temperatures; and
   a data processing unit, comprising:
      a memory configured to store program instructions; and
      an on-board data processor communicatively coupled to the memory and the measurement circuit, wherein the on-board data processor is programmed to execute the program instructions to receive, from the measurement circuit, the dielectric excitation responses of the gas sensing element at each of the multiple temperatures while the gas sensing element contacts the fluid sample in real-time.

2. The gas sensor system of claim 1, wherein the on-board data processor is configured to select at least two of the dielectric excitation responses of the gas sensing element at each of the multiple temperatures to differentiate the at least two gases in the fluid sample.

3. The gas sensor system of claim 2, wherein the at least two selected dielectric excitation responses are impedance responses of the gas sensing element at each of the multiple temperatures.

4. The gas sensor system of claim 2, wherein the at least two selected dielectric excitation responses are not resistance responses.

5. The gas sensor system of claim 2, wherein the on-board data processor is configured to differentiate the at least two gases by determining respective classifications, respective concentrations, or a combination thereof, of the at least two gases in the fluid sample based on the at least two selected dielectric excitation responses of the gas sensing element at each of the multiple temperatures.

6. The gas sensor system of claim 1, wherein the measurement circuit is configured to measure the dielectric excitation responses of the gas sensing element at multiple pre-selected frequencies at each of the multiple temperatures.

7. The gas sensor system of claim 6, wherein, at each pre-selected frequency and at each of the multiple temperatures, the measurement circuit is configured to measure dielectric excitation responses of the gas sensing element that are correlated with concentrations of a particular gas of a plurality of gases in the fluid sample.

8. The gas sensor system of claim 1, wherein the gas sensing element comprises:

a substrate, wherein the heating element is coupled to the substrate;

a single sensing material disposed on the substrate and configured to contact the fluid sample; and electrodes coupled to the single sensing material and electrically coupled to the measurement circuit, wherein the electrodes are configured to apply, to the single sensing material, the dielectric excitation provided by the measurement circuit, and wherein the measurement circuit is configured to measure the dielectric excitation responses of the single sensing material at each of the multiple temperatures via the electrodes.

9. The gas sensor system of claim 8, wherein the single sensing material is a semiconducting metal oxide material.

10. The gas sensor system of claim 1, wherein the multiple temperatures comprise at least two different temperatures.

11. The gas sensor system of claim 1, wherein the at least two gases in the fluid sample comprises at least two analyte gases or at least one analyte gas and at least one interfering gas.

* * * * *